US012195799B2

(12) United States Patent
Oliphant et al.

(10) Patent No.: US 12,195,799 B2
(45) Date of Patent: *Jan. 14, 2025

(54) RISK CALCULATION FOR EVALUATION OF FETAL ANEUPLOIDY

(71) Applicant: Ariosa Diagnostics, Inc., San Jose, CA (US)

(72) Inventors: Arnold Oliphant, San Jose, CA (US); Andrew Sparks, San Jose, CA (US); Eric Wang, Milpitas, CA (US); Craig Struble, Glendale, WI (US)

(73) Assignee: Ariosa Diagnostics, Inc., San Jose, CA (US)

( * ) Notice: Subject to any disclaimer, the term of this patent is extended or adjusted under 35 U.S.C. 154(b) by 1235 days.

This patent is subject to a terminal disclaimer.

(21) Appl. No.: 16/915,944

(22) Filed: Jun. 29, 2020

(65) Prior Publication Data

US 2021/0189493 A1 Jun. 24, 2021

Related U.S. Application Data

(63) Continuation of application No. 16/058,849, filed on Aug. 8, 2018, now Pat. No. 10,718,024, which is a continuation of application No. 14/853,848, filed on Sep. 14, 2015, now Pat. No. 10,718,019, which is a continuation of application No. 13/689,417, filed on Nov. 29, 2012, now abandoned, which is a continuation of application No. 13/338,963, filed on Dec. 28, 2011, now Pat. No. 8,700,338, which is a continuation-in-part of application No. 13/316,154, filed on Dec. 9, 2011, now abandoned.

(60) Provisional application No. 61/436,135, filed on Jan. 25, 2011.

(51) Int. Cl.
| | | |
|---|---|---|
| *G01N 33/48* | (2006.01) | |
| *C12Q 1/6806* | (2018.01) | |
| *C12Q 1/686* | (2018.01) | |
| *C12Q 1/6883* | (2018.01) | |
| *G01N 33/50* | (2006.01) | |
| *G16B 20/00* | (2019.01) | |
| *G16B 20/10* | (2019.01) | |
| *G16B 20/20* | (2019.01) | |
| *G16B 20/40* | (2019.01) | |
| *G16B 30/00* | (2019.01) | |

(52) U.S. Cl.
CPC ......... *C12Q 1/6883* (2013.01); *C12Q 1/6806* (2013.01); *C12Q 1/686* (2013.01); *G16B 20/00* (2019.02); *G16B 20/10* (2019.02); *G16B 20/20* (2019.02); *G16B 20/40* (2019.02); *G16B 30/00* (2019.02); *C12Q 2600/156* (2013.01)

(58) Field of Classification Search
CPC .... C12Q 1/6883; C12Q 1/6806; C12Q 1/686; C12Q 2600/156; G16B 20/00; G16B 30/00
See application file for complete search history.

(56) References Cited

U.S. PATENT DOCUMENTS

| | | |
|---|---|---|
| 4,683,195 A | 7/1987 | Mullis et al. |
| 4,988,617 A | 1/1991 | Landegren et al. |
| 5,143,854 A | 9/1992 | Pirrung et al. |
| 5,242,794 A | 9/1993 | Whiteley et al. |
| 5,270,184 A | 12/1993 | Walker et al. |
| 5,399,491 A | 3/1995 | Kacian et al. |
| 5,409,818 A | 4/1995 | Davey et al. |
| 5,413,909 A | 5/1995 | Bassam et al. |
| 5,422,252 A | 6/1995 | Walker et al. |
| 5,437,975 A | 8/1995 | McClelland |
| 5,494,810 A | 2/1996 | Barany et al. |
| 5,547,839 A | 8/1996 | Dower et al. |
| 5,554,517 A | 9/1996 | Davey et al. |
| 5,578,832 A | 11/1996 | Trulson et al. |
| 5,631,734 A | 5/1997 | Stern et al. |
| 5,648,245 A | 7/1997 | Fire et al. |
| 5,800,992 A | 9/1998 | Fodor et al. |
| 5,808,041 A | 9/1998 | Padhye et al. |
| 5,830,711 A | 11/1998 | Barany et al. |
| 5,834,758 A | 11/1998 | Trulson et al. |
| 5,856,092 A | 1/1999 | Dale et al. |
| 5,861,245 A | 1/1999 | McClelland et al. |
| 5,871,928 A | 2/1999 | Fodor et al. |
| 5,874,219 A | 2/1999 | Rava et al. |
| 5,876,924 A | 3/1999 | Zhang et al. |
| 5,888,740 A | 3/1999 | Han |
| 5,898,071 A | 4/1999 | Hawkins |

(Continued)

FOREIGN PATENT DOCUMENTS

| | | |
|---|---|---|
| GB | 2299166 | 9/1996 |
| GB | 970444.0 | 3/1997 |

(Continued)

OTHER PUBLICATIONS

Rebrikov et al. Real-time PCR: A review of approaches to data analysis. Applied Biochemistry and Microbiology, vol. 42, pp. 455-463. (Year: 2006).*

(Continued)

*Primary Examiner* — Russell S Negin
(74) *Attorney, Agent, or Firm* — Mintz, Levin, Cohn, Ferris, Glovsky and Popeo, P.C.

(57) ABSTRACT

The present invention provides processes for determining accurate risk probabilities for fetal aneuploidies. Specifically, the invention provides non-invasive evaluation of genomic variations through chromosome-selective sequencing and non-host fraction data analysis of maternal samples.

20 Claims, 5 Drawing Sheets

(56) References Cited

U.S. PATENT DOCUMENTS

| | | |
|---|---|---|
| 5,902,723 A | 5/1999 | Dower et al. |
| 5,936,324 A | 8/1999 | Montagu |
| 5,952,170 A | 9/1999 | Stroun et al. |
| 5,981,956 A | 11/1999 | Stern |
| 6,025,601 A | 2/2000 | Trulson et al. |
| 6,027,889 A | 2/2000 | Barany et al. |
| 6,045,996 A | 4/2000 | Cronin et al. |
| 6,054,564 A | 4/2000 | Barany et al. |
| 6,063,603 A | 5/2000 | Davey et al. |
| 6,090,555 A | 7/2000 | Fiekowsky et al. |
| 6,136,229 A | 10/2000 | Cui et al. |
| 6,141,096 A | 10/2000 | Stern et al. |
| 6,143,495 A | 11/2000 | Lizardi et al. |
| 6,156,504 A | 12/2000 | Gocke et al. |
| 6,185,030 B1 | 2/2001 | Overbeck |
| 6,201,639 B1 | 3/2001 | Overbeck |
| 6,210,891 B1 | 4/2001 | Nyren et al. |
| 6,218,803 B1 | 4/2001 | Montagu et al. |
| 6,225,625 B1 | 5/2001 | Pirrung et al. |
| 6,258,540 B1 | 7/2001 | Lo et al. |
| 6,268,148 B1 | 7/2001 | Barany et al. |
| 6,309,824 B1 | 10/2001 | Drmanac |
| 6,310,199 B1 | 10/2001 | Smith et al. |
| 6,312,892 B1 | 11/2001 | Barany et al. |
| 6,329,179 B1 | 12/2001 | Kopreski |
| 6,342,387 B1 | 1/2002 | Hayashizaki et al. |
| 6,386,749 B1 | 5/2002 | Watts et al. |
| 6,391,623 B1 | 5/2002 | Besemer et al. |
| 6,401,267 B1 | 6/2002 | Drmanac |
| 6,410,276 B1 | 6/2002 | Burg et al. |
| 6,506,594 B1 | 1/2003 | Barany et al. |
| 6,534,262 B1 | 3/2003 | McKernan et al. |
| 6,534,293 B1 | 3/2003 | Barany et al. |
| 6,562,573 B2 | 5/2003 | Halaka |
| 6,573,103 B1 | 6/2003 | Wald |
| 6,576,453 B2 | 6/2003 | Barany et al. |
| 6,797,470 B2 | 9/2004 | Barany et al. |
| 6,828,100 B1 | 12/2004 | Ronghi |
| 6,833,246 B2 | 12/2004 | Balasubramanian |
| 6,852,487 B1 | 2/2005 | Barany et al. |
| 6,858,412 B2 | 2/2005 | Willis et al. |
| 6,864,052 B1 | 3/2005 | Drmanac et al. |
| 6,911,345 B2 | 6/2005 | Quake et al. |
| 6,914,137 B2 | 7/2005 | Baker |
| 6,927,028 B2 | 8/2005 | Dennis et al. |
| 6,949,370 B1 | 9/2005 | Barany et al. |
| 6,977,162 B2 | 12/2005 | Barany et al. |
| 7,014,994 B1 | 3/2006 | Barany et al. |
| 7,083,917 B2 | 8/2006 | Barany et al. |
| 7,097,980 B2 | 8/2006 | Barany et al. |
| 7,166,434 B2 | 1/2007 | Barany et al. |
| 7,198,894 B2 | 4/2007 | Barany et al. |
| 7,208,274 B2 | 4/2007 | Dhallan |
| 7,232,656 B2 | 6/2007 | Balasubramanian |
| 7,244,233 B2 | 7/2007 | Krantz et al. |
| 7,244,831 B2 | 7/2007 | Barany et al. |
| 7,312,039 B2 | 12/2007 | Barany et al. |
| 7,315,787 B2 | 1/2008 | Orlandi et al. |
| 7,320,865 B2 | 1/2008 | Barany et al. |
| 7,332,277 B2 | 2/2008 | Dhallan |
| 7,332,285 B2 | 2/2008 | Barany et al. |
| 7,343,190 B2 | 3/2008 | Krantz et al. |
| 7,358,048 B2 | 4/2008 | Krantz et al. |
| 7,364,858 B2 | 4/2008 | Barany et al. |
| 7,429,453 B2 | 9/2008 | Barany et al. |
| 7,442,506 B2 | 10/2008 | Dhallan |
| 7,455,965 B2 | 11/2008 | Barany et al. |
| 7,459,311 B2 | 12/2008 | Nyren et al. |
| 7,527,929 B2 | 5/2009 | McKernan et al. |
| 7,556,924 B2 | 7/2009 | Barany et al. |
| 7,582,420 B2 | 9/2009 | Oliphant et al. |
| 7,598,060 B2 | 10/2009 | Dhallan |
| 7,601,491 B2 | 10/2009 | Collis et al. |
| 7,622,281 B2 | 11/2009 | Ronaghi et al. |
| 7,645,576 B2 | 1/2010 | Lo et al. |
| 7,648,824 B2 | 1/2010 | Nyren et al. |
| 7,700,323 B2 | 4/2010 | Willis et al. |
| 7,709,194 B2 | 5/2010 | Lo et al. |
| 7,709,201 B2 | 5/2010 | Barany et al. |
| 7,718,367 B2 | 5/2010 | Lo et al. |
| 7,718,370 B2 | 5/2010 | Dhallan |
| 7,727,720 B2 | 6/2010 | Dhallan |
| 7,727,727 B2 | 6/2010 | Collis |
| 7,754,428 B2 | 7/2010 | Lo et al. |
| 7,780,600 B2 | 8/2010 | Krantz et al. |
| 7,799,531 B2 | 9/2010 | Mitchell et al. |
| 7,807,431 B2 | 10/2010 | Barany et al. |
| 7,888,017 B2 | 2/2011 | Quake et al. |
| 7,901,884 B2 | 3/2011 | Lo et al. |
| 7,989,614 B2 | 8/2011 | Deggerdal et al. |
| 8,008,018 B2 | 8/2011 | Quake et al. |
| 8,195,415 B2 | 6/2012 | Fan et al. |
| 8,296,076 B2 | 10/2012 | Fan et al. |
| 8,318,430 B2 | 11/2012 | Chuu et al. |
| 8,700,338 B2 | 4/2014 | Oliphant et al. |
| 8,756,020 B2 | 6/2014 | Struble et al. |
| 9,567,639 B2 | 2/2017 | Oliphant et al. |
| 10,718,019 B2 | 7/2020 | Oliphant et al. |
| 10,718,024 B2 | 7/2020 | Oliphant et al. |
| 2001/0051341 A1 | 12/2001 | Lo et al. |
| 2002/0045176 A1 | 4/2002 | Lo et al. |
| 2002/0132241 A1 | 9/2002 | Fan et al. |
| 2002/0160361 A1 | 10/2002 | Loehrlein et al. |
| 2003/0003459 A1 | 1/2003 | Stahl |
| 2003/0044388 A1 | 3/2003 | Dennis et al. |
| 2003/0054386 A1 | 3/2003 | Antonarakis et al. |
| 2003/0064366 A1 | 4/2003 | Hardin et al. |
| 2003/0108913 A1 | 6/2003 | Schouten |
| 2003/0143599 A1 | 7/2003 | Makarov et al. |
| 2004/0009518 A1 | 1/2004 | Lo et al. |
| 2004/0086864 A1 | 5/2004 | Lo et al. |
| 2004/0101835 A1 | 5/2004 | Willis et al. |
| 2004/0137470 A1 | 7/2004 | Dhallan |
| 2004/0203037 A1 | 10/2004 | Lo et al. |
| 2004/0214175 A9 | 10/2004 | McKernan et al. |
| 2005/0095618 A1 | 5/2005 | Tsui et al. |
| 2005/0100939 A1 | 5/2005 | Namsaraev et al. |
| 2005/0191656 A1 | 9/2005 | Drmanac et al. |
| 2006/0121452 A1 | 6/2006 | Dhallan |
| 2006/0204495 A1 | 9/2006 | Zang |
| 2006/0252068 A1 | 11/2006 | Lo et al. |
| 2006/0252071 A1 | 11/2006 | Lo et al. |
| 2006/0275789 A1 | 12/2006 | Willis et al. |
| 2007/0087345 A1 | 4/2007 | Olson-Munoz et al. |
| 2007/0172873 A1 | 7/2007 | Brenner et al. |
| 2007/0178478 A1 | 8/2007 | Dhallan |
| 2007/0202525 A1 | 8/2007 | Quake et al. |
| 2007/0207482 A1 | 9/2007 | Church et al. |
| 2007/0275402 A1 | 11/2007 | Lo et al. |
| 2008/0020390 A1 | 1/2008 | Mitchell et al. |
| 2008/0081338 A1 | 4/2008 | Lo et al. |
| 2008/0090239 A1 | 4/2008 | Shoemaker et al. |
| 2008/0096766 A1 | 4/2008 | Lee |
| 2008/0243398 A1 | 4/2008 | Lo et al. |
| 2008/0138809 A1 | 6/2008 | Kapur et al. |
| 2008/0206749 A1 | 8/2008 | Lo et al. |
| 2009/0018024 A1 | 1/2009 | Church et al. |
| 2009/0029377 A1 | 1/2009 | Lo et al. |
| 2009/0048124 A1 | 2/2009 | Leamon et al. |
| 2009/0061425 A1 | 3/2009 | Lo et al. |
| 2009/0087847 A1 | 4/2009 | Lo et al. |
| 2009/0099041 A1 | 4/2009 | Church et al. |
| 2009/0155776 A1 | 6/2009 | Lo et al. |
| 2010/0105049 A1 | 4/2010 | Ehrich et al. |
| 2010/0105052 A1 | 4/2010 | Drmanac et al. |
| 2010/0112575 A1 | 5/2010 | Fan |
| 2010/0112590 A1 | 5/2010 | Lo et al. |
| 2010/0120076 A1 | 5/2010 | Braun et al. |
| 2010/0136529 A1 | 6/2010 | Shoemaker et al. |
| 2010/0184043 A1 | 7/2010 | Mitchell et al. |
| 2010/0184044 A1 | 7/2010 | Mitchell et al. |
| 2010/0184210 A1 | 7/2010 | Rossmanith et al. |
| 2010/0267034 A1 | 10/2010 | Lo et al. |
| 2010/0291571 A1 | 11/2010 | Stoughton et al. |

(56) References Cited

U.S. PATENT DOCUMENTS

| | | |
|---|---|---|
| 2010/0291572 A1 | 11/2010 | Stoughton et al. |
| 2011/0003293 A1 | 1/2011 | Stoughton et al. |
| 2011/0027771 A1 | 2/2011 | Deng |
| 2011/0039724 A1 | 2/2011 | Lo et al. |
| 2011/0059451 A1 | 3/2011 | Mitchell et al. |
| 2011/0086357 A1 | 4/2011 | Lo et al. |
| 2011/0105353 A1 | 5/2011 | Lo et al. |
| 2011/0117548 A1 | 5/2011 | Mitchell et al. |
| 2011/0124518 A1 | 5/2011 | Cantor |
| 2011/0143342 A1 | 6/2011 | Lo et al. |
| 2011/0151442 A1 | 6/2011 | Fan et al. |
| 2011/0171638 A1 | 7/2011 | Stoughton et al. |
| 2011/0172111 A1 | 7/2011 | Cantor |
| 2011/0177517 A1 | 7/2011 | Rava et al. |
| 2011/0178719 A1 | 7/2011 | Rabinowitz |
| 2011/0183330 A1 | 7/2011 | Lo et al. |
| 2011/0201507 A1 | 8/2011 | Rava et al. |
| 2011/0224087 A1 | 9/2011 | Quake et al. |
| 2011/0230358 A1 | 9/2011 | Rava et al. |
| 2011/0245085 A1 | 10/2011 | Rava et al. |
| 2011/0276277 A1 | 11/2011 | Lo et al. |
| 2011/0288780 A1 | 11/2011 | Rabinowitz |
| 2011/0312503 A1 | 12/2011 | Chuu |
| 2012/0003650 A1 | 1/2012 | Lo et al. |
| 2012/0010085 A1 | 1/2012 | Rava |
| 2012/0034603 A1 | 2/2012 | Oliphant et al. |
| 2012/0034685 A1 | 2/2012 | Sparks et al. |
| 2012/0040859 A1 | 2/2012 | Sparks et al. |
| 2012/0100548 A1 | 4/2012 | Rava et al. |
| 2012/0108460 A1 | 5/2012 | Quake et al. |
| 2012/0165203 A1 | 6/2012 | Quake et al. |
| 2012/0184449 A1 | 7/2012 | Hixson |
| 2012/0190557 A1 | 7/2012 | Oliphant et al. |
| 2012/0191358 A1 | 7/2012 | Oliphant et al. |
| 2012/0191367 A1 | 7/2012 | Stuelpnagel et al. |
| 2012/0219950 A1 | 8/2012 | Oliphant et al. |
| 2012/0225798 A1 | 9/2012 | Cantor et al. |
| 2012/0237928 A1 | 9/2012 | Rava et al. |
| 2012/0264115 A1 | 10/2012 | Rava |
| 2012/0264121 A1 | 10/2012 | Rava et al. |
| 2012/0270739 A1 | 10/2012 | Rava et al. |
| 2013/0029852 A1 | 1/2013 | Rava et al. |
| 2013/0040375 A1 | 2/2013 | Sparks et al. |
| 2013/0089863 A1 | 4/2013 | Oliphant et al. |
| 2013/0122500 A1 | 5/2013 | Sparks et al. |
| 2013/0172211 A1 | 7/2013 | Oliphant et al. |
| 2013/0172212 A1 | 7/2013 | Oliphant et al. |
| 2013/0172213 A1 | 7/2013 | Oliphant et al. |
| 2013/0210640 A1 | 8/2013 | Sparks et al. |
| 2013/0288244 A1 | 10/2013 | Deciu et al. |
| 2013/0288252 A1 | 10/2013 | Sparks et al. |
| 2014/0024538 A1 | 1/2014 | Zahn et al. |
| 2014/0342940 A1 | 11/2014 | Oliphant et al. |
| 2016/0002729 A1 | 1/2016 | Oliphant et al. |
| 2017/0121769 A1 | 5/2017 | Sparks et al. |
| 2017/0145510 A1 | 5/2017 | Oliphant et al. |

FOREIGN PATENT DOCUMENTS

| | | |
|---|---|---|
| GB | 9704444.0 | 3/1997 |
| WO | WO-87/006270 A1 | 10/1987 |
| WO | WO-90/06995 A1 | 6/1990 |
| WO | WO-98/39474 A1 | 9/1998 |
| WO | WO-99/47964 A1 | 9/1999 |
| WO | WO-00/04193 A1 | 1/2000 |
| WO | WO-00/56927 | 9/2000 |
| WO | WO-2003/038120 | 5/2003 |
| WO | WO-2007/100243 A1 | 9/2007 |
| WO | WO-2007/126377 A1 | 11/2007 |
| WO | WO-2008/118998 | 10/2008 |
| WO | WO-2009-036525 | 3/2009 |
| WO | WO-2009/102632 | 8/2009 |
| WO | WO-2011/066476 | 6/2011 |
| WO | WO-2011/090556 A1 | 7/2011 |
| WO | WO-2011/090557 A1 | 7/2011 |
| WO | WO-2011/090558 A1 | 7/2011 |
| WO | WO-2012/019187 | 2/2012 |
| WO | WO-2012/019193 | 2/2012 |
| WO | WO-2012/019200 | 2/2012 |
| WO | WO-2012/088456 | 6/2012 |
| WO | WO-2012/102945 A1 | 8/2012 |
| WO | WO-2012/103031 | 8/2012 |
| WO | WO-2013/009175 A1 | 1/2013 |
| WO | WO-2013/192292 A1 | 12/2013 |
| WO | WO-2016/018986 A1 | 2/2016 |

OTHER PUBLICATIONS

Mikhaylov, V.M. et al., (Jun. 1989). "Changes in the quantity and synthesis of DNA in the nuclei of large decidual cells of rats in the course of their differentiation", Tsitologiya (Cytology) 31(6):677-683.

Moreno and Gomella, (Nov. 1998). "Circulating Prostate Cancer Cells Detected by Reverse Transcription-Polymerase Chain Reaction (RT-PCR: What do they mean?", Cancer Control Journal, 5(6):507-512.

Mulcahy, H.E. et al. (Apr. 2000). "Plasma DNA K-ras Mutations in Patients with Gastrointestinal Malignancies," Annals New York Academy of Sciences, 906:25-28.

Abadia-Molina, et al., "Immune phenotype and cytotoxic activity of lymploycytes from human term decidua against trophoblast", J. of Reproductive Immunology, n31:109-23 (1996).

Advisory Action Received on Jan. 29, 2013 for U.S. Appl. No. 13/293,419 (inventor A. Sparks, filed Nov. 10, 2011), entire document.

Agostini, et al., "Circulating cell-free DNA: a promising marker of pathologic tumor response in rectal cancer patients receiving pre-operative chemotherapy", Ann. Surg. Oncol., 18(9):2461-68 (2011).

Alexandrov, et al., (May 11, 1993). "Definition of a new alpha satellite suprachromosomal family characterized by monomeric organization", Nucleic Acids Research, 21(9):2209-2215.

Anker, et al., Information carried by the DNA release by antigen-stimulated lymphocytes:, Immunology, 37:753-63 (1979).

Anker, et al., "K-ras Mutations are found in DNA extreacted from the plasma of patients with colorectal cancer," Gastroenterology, 112:1114-20 (1997).

Anker, et al., "Spontaneous Release of DNA by Human Blood Lymphocytes as Shown in an in Vitro System", Cancer Research, 35:2375-82 (1975).

Arnheim, et al., "Molecular evidence for genetic exchanges among ribosomal genes on nonhomologous chromosomes in man and apes", PNAS USA, 77(12):7323-27 (1980).

Ashoor, et al., "Chromosome-selective sequencing of maternal plasma cell-free DNA for first-trimester detection of trisomy 21 and trisomy 18", Am. J. of Obstet. Gynecol., (2012), doi: 10.1016/j.ajog.2012.01.029.

Ashoor, et al., Fetal Fraction in Maternal Plasma Cell-Free DNA at 11-13 Weeks' Gestation: Effect of Maternal and Fetal Factors, Fetal Dian Ther D01:10.1159/000337373 (Pub'd online May 4, 2012).

Australian Patent Examination Report No. 1 dated Feb. 20, 2014 for 2011285512, entire document.

Australian Patent Examination Report No. 1 dated Feb. 7, 2014 for 2011285477, entire document.

Australian Patent Examination Report No. 1 dated Mar. 4, 2014 for 2011285518, entire document.

Avent, N.D. (2008). "RHD genotyping from maternal plasma: guidelines and technical challenges," Methods in Molecular Biology 444:185-201.

Bandyopadhyay, et al, "Identification and characterization of satellite III subfamilies to the acrocentric chromosomes", Chromosome Research, 9:223-33 (2001).

Batzer and Deininger, "ALU Repeats and Human Genomic Diversity", Nature, 3:370-79 (2002).

Beard, "Embryological Aspects and Etiology of Carcinoma", The Lancet, Jun. 21, 1902, pp. 1758-1761.

(56) References Cited

OTHER PUBLICATIONS

Belokhvostov, et al., "Changes in the Fractional Composition of the Nucleic Acids in Blood Serum upon Rediation Damage Early Stage Abnormalities Following Gamma-Irradiation of Rats", Tsitologiia (Cytology) 1986.
Bianchi, "Isolation of fetal DNA from nucleated erythrocytes in maternal blood", PNAS USA, 87:3279-83 (1990).
Bianchi, "PCR Quantitation of Fetal Cells in Maternal Blood in Normal and Aneuploid Pregnancies", Am J. Hum. Genet., 61:822-29 (1997).
Bianchi, "Prenatal diagnosis by analysis of fetal cells in maternal blood", J. of Pediatrics, 127(6):847-56 (1995).
Bianchi, et al., "Large Amounts of Cell-free DNAS Are Present in Amniotic Fluid", Clin. Chem., 47(10) 1867-69 (2001).
Biran, "On the Oncodevelopmental Rold of Human Imprinted Genes", 43:119-23 (1994).
Blaschke and Rappold, "The Pseudoautosomal regions, SHOX and disease", Curr. Opin. Gene. Dev., 16(3):23-29 (2006).
Bodurtha and Strauss, "Genomics and Prenatal Care", New Eng. J. of Medicine, 366:64-73 (2012).
Bombard, et al., "Fetal RHD genotype detection from circulating cell-free DNA in maternal plasma in non-sensitized RhD negative women", Prenat Diagn, 31:802-08 (2011).
Boyle, E.A. et al (Sep. 15, 2014, e-published May 26, 2014). "MIPgen: optimized modeling and design of molecular inversion probes for targeted resequencing," Bioinformatics 30(18):2670-2672.
Bradstock, et al., "Functional and phenotypic assessment of neonatal human leucocytes expressing natural killer cell-associated antigen", Immunology and Cell Biology (71:535-42 (1993).
Bustamante-Aragones et al. (Mar. 2010). "Noninvasive prenatal diagnosis using ccffDNA in maternal blood:state of the art," *Expert Reviews in Molecular Diagnostics* 10(2):197-205.
Camaschella, et al., "Prenatal Diagnosis of Fetal Hemoglobin Lepore-Boston Disease on Maternal Peripheral Blood", Blood, 75(11):2102-06 (1990).
Campbell, et al., "Subclonal phylogenetic structions in cancer revealed by ultra-deep sequencing", PNAS, 105(35):13081-86 (2008).
Cappuzzo, et al., "Epidermal growth factor receptor gene and protein and gefitinib sensitivity in non-small-cell lung cancer", J. Nati Cancer Inst., 97(9):643-55 (2005).
Centre for Genomics Education, "Changes to Chromosome Structure—Translocations", The Australasian Genetics Resource Book, www.aenetics corn, pp. 1-5 (2007).
Chen, et al., "Microsatellite alterations in plasma DNA of small cell lung cancer patients", Nature Medicine, 2(9):1033-35 (1996).
Chen, et al., "Noninvasive prenatal diagnosis of fetal trisomy 18 and trisomy 13 by maternal plasma DNA sequencing", PLos One, 6:e21791 (2011).
Chim, et al., "Detection of the placental epigenetic signature of the maspin gene in maternal plasma", PNAS USA, 102(41):14753-58 (2005).
Chinen, P.A. et al. (Nov. 2010), e-published Apr. 20, 2010). "Noninvasive determination of fetal rh blood group, D antigen status by cell-free DNA analysis in maternal plasma: experience in a Brazilian population," *Am J Perinatol* 27(1):759-762.
Chiu and Lo, "Non-invasive prenatal diagnosis by fetal nucleic acid analysis in maternal plasma: the coming of age", Semin. Fetal Neonatal Med., 16(2):88-93 (2011).
Chiu, et al., "Effects of Blood-Processing Protocols on Fetal and Total DNA Quantification in Maternal Plasma", Clin. Chem., 47(9):1607-1613 (2001).
Chiu, et al., "Noninvasive prenatal diagnosis of fetal chromosomal aneuploidy by massively parallel genomic sequencing of DNA in maternal plasma", PNAS USA 105:20458-63 (2008), 17 pages supporting information.
Chiu, et al., "Maternal plasma DNA analysis with massively parallel sequencing by ligation for noninvasive prenatal diagnosis of trisomy 21", Clinical Chemistry 56:459-63 (2010).

Chiu, et al., "Non-invasive prenatal assessment of trisomy 21 by multiplexed maternal plasma DNA sequencing: large scale validity study", Br Med J. 342:c7401 (2011).
Chiu, et al., "Non-invasive prenatal diagnosis by single molecule counting technologies", Trends in Genomics, 25(7):324-31 (2009).
Choo, et al., "A Chromosome 14-specific Human Satellite III DNA Subfamily That Shows Variable Presence on Different Chromosomes 14", Am J. Hum. Genet., 50:706-16 (1992).
Choo, et al., "A homologous subfamily of satellite III DNA on human chromosomes 14 and 22", Nucleic Acids Research, 18(19):5641-47 (1990).
Chromosome 14 Map (Mar. 14, 1996). The Genethon Human Genetic Linkage Map, Collections, Supplements, Nature, 3 pages.
Chu, et al., "A novel approach toward the challenge of accurately quantifying fetal DNA in maternal plasma", Prenat. Diag., 30:1226-29 (2010).
Ciccodicola, et al., "Differentially regulated and evolved genes in the fully sequences Xq/Yq pseudoautosomal region", Hum. Mol. Genet., 9(3):395-401 (2000).
Cicuttini and Boyd, "Hemopoietic and Lymphoid Progenitro Cells in Human Umbilical Cord Blood", Developmental Immunology, 4:1-11 (1994).
Cirigiliano, et al., "Clinical application of multiplex quantitative fluorescent polymerase chain reaction QF-PCR for the repaid prenatal detection of common chromosome aneuploidies", Molecular Human Reproduction, 7(10):1001-06 (2001).
Cirigiliano, et al., "Rapid prenatal diagnosis of common chromosome aneuploidies by QF-PCR, results of 9 years of clinical experience", Prenatal diagnosis, 29:40-49 (2009).
Cockwell, et al., "Distribution of the D15A1 copy number polymorphism", European J. of Hum. Genet., 15:441-45 (2007).
Conover, Practical Nonparametric Statistics, pp. 295-01 (John Wiley & Sons, NY)(1971).
Costa, et al., "New strategy for prenatal diagnosis of X-linked disorders", N. Engl J. Med., 346:1502 (2002).
Datta, et al., "Sensitive Detection of Occult Breast Cancer by the Reverse-Transcriptase Polymerase Chain Reaction", J. of Clinical Oncology, 12(3): 475-82 (1994).
Dear, et al., "A High-Resolution Metric HAPPY Map of Human Chromosome 14" Genmoics, 48 232-41 (1998).
Dennin, "DNA of Free and Complexed Origin in Human Plasma: Concentration and Length Distribution", Klin. Wochenschr., 57:451-56 (1979).
Dhallan, et al., "A non-invasive test for prenatal diagnosis based on fetal DNA present in maternal blood: a preliminary study", Lancet, 369(9560):474-81 (2007).
Dobrzycka, et al., "Circulating free DNA and p53 antibodies in plasma of patients with ovarian epithelial cancers", Annals of Oncology, 22:1133-40 (2011).
Dobrzycka, et al., "Prognostic significance of VEGF and its receptors in endometrioid endometrial cancer", Ginekol Pol. 81(6):422-25 (2010).
Duan, et al., "PstSNP-HapMap3: a database of SNPs with high population differentiation for HapMap3", Bioinformation, 3(3):139-41 (2008).
Earle, et al., "Identification of DNA Sequences Flanking the Breakpoin of Human t(14q21q) Robertsonian Translocations", Am J. Hum Genet., 50:717-24 (1992).
Ehrich, et al., "Noninvasive detection of fetal trisomy 21 by sequencing of fetal DNA in maternal blood: a study in a clinical setting", Am J. Obstet Gynecol, 2011:204:205 el-11 (2011).
Enders, et al., "Fetal morbidity and mortality after acute human parvovirus B19 infection in pregnancy: prospective evaluation of 1018 cases", Prenatal Diagnosis, 24:513-18 (2004).
EPO Examination Report dated Nov. 21, 2013 for App. No. 11745880. 2, entire document.
EPO Examination Report dated Nov. 21, 2013 for App. No. 11745881. 1, entire document.
EPO Examination Report dated Nov. 28, 2013 for App. No. 11745883. 6, entire document.
Fan, et al., "Analysis of the Size Distributions of Fetal and Maternal Cell-Free DNA by Paired-End Sequencing", Clin. Chem., 56(8):1279-80 (2010).

(56) References Cited

OTHER PUBLICATIONS

Fan, et al., "Noninvasive diagnosis of fetal aneuploidy by shotgun sequencing DNA from maternal blood", PNAS USA, 105(42):16266-71 (2008).
Fan, et al., "Sensitivity of noninvasive prenatal detection of fetal aneuploidy from maternal plasma using shotgun sequencing is limited only by counting statistics", PLoS One, 5:e10439 (2010).
Fejgin, et al., "Fetal cells in the uterine cervix: a source for early non-invasive prenatal diagnosis", Prenat. Diag., 21:619-21 (2001).
Final Office Action Received on Jul. 8, 2013 for U.S. Appl. No. 13/689,206 (inventor A. Oliphant, filed Nov. 30, 2012), entire document.
Final Office Action Received on Oct. 12, 2012 for U.S. Appl. No. 13/293,419 (inventor A. Sparks, filed Nov. 10, 2011), entire document.
Finning, et al., "Effect of high throughput RHD typing of fetal DNA in maternal plasma on use of anti-RhD immunoglobulin in RhD negative pregnant women: prospective feasibility study", Br Med J., 336:816-18 (2008).
Fisher, et al., "Genetic evidence that placental site trophoblastic tumours can originate from a hydatidiform mole or a normal conceptus", Br. J. Cancer, 65:355-58 (1992).
Fournie, et al., "Plasma DNA as Cell Death Marker in Elderly Patients", Gerontology, 39:215-221 (1993).
Fowke, Genetic analysis of human DNA recovered from minute amounts of serum and plasma, J. of Immunol. Meth., 180:45-51 (1995).
Geifman-Holzman, et al., "Fetal RhD genotyping in fetal cells flow sorted from maternal blood", Am. J.Obstet. Gynecol., 174(3):818-22 (1996).
Ghanta, S. et al. (Oct. 8, 2010). "Non-invasive prenatal detection of trisomy 21 using tandem single nucleotide polymorphisms," *PlosOne* 5(10):e13184.
Ghossein, et al.. "Detection of Circulating Tumor Cells in Patients with Localized and Metastatic Prostatic Carcinoma Clinical Implications", J. of Clin. Oncology, 13(5):1995-200 (1995).
Gold, "Cancer and Pregnancy: Parallels in Growth, Invasion, and Immune Modulation and Implicationsa for Cancer Therapeutic Agents", Mayo Clin. Proc., 84(11):985-1000 (2009).
Gosden, et al., "Satellite DNA Sequences in the Human Acrocentric Chromosomes: Information from Translocations and Heteromorphisms", Am. J. Hum. Genet., 33:243-51 (1981).
Guo, Q. et al. (Sep. 2010, e-published Jul. 9, 2010). "Simultaneous detection of trisomies 13, 18, and 21 with multiplex ligation-dependent probe amplification-based real-time PCR," Clin Chem 56(9):1451-1459.
Greeley, et al., "Get ready for the flood of fetal gene screening", Nature, 469:289-91 (2011).
Green, et al., "Gestational Trophoblastic Disease: A Spectrum of Radiologic Diagnosis", Radiographics, 16(6):1371-84 (1996).
Gribben, et al., "Detection of Residual Lymphoma Cells by Polymerase Chain Reaction in Peripheral Blood is Significantly Less Predictive for Relapse Than Detection in Bone Marrow", Blood, 83(12):3800-07 (1994).
Guatelli, et al., "Isothermal, in vitro amplification of nucleic acids by a multienzyme reaction modeled after retroviral replication", PNAS USA, 87(5):1874—(1990).
Han, et al., "Molecular Chytogenetic Characterization of 17 rob(13q14q) Robertsonian Translocations by FISH, Narrowing the Region Containing the Breakpoints", Am J. Hum. Genet., 55:960-67 (1994).
Hardenbol et al., Multiplexed genotyping with sequence-tagged molecular inversion probes. Nat Biotechnol. Jun. 2003;21(6):673-8.
Hardingham, et al., "Detection of Circulating Tumor Cells in Colorectal Cancer by Immunogead-PCR is a Sensitive Prognostic marker for Relapse of Disease", Molecular Medicine, 1(7):789-94 (1995).
Harrell, Regression modeling strategies, §§9.2.2 and 1.10.5 (Springer Vertag)(2001).
Hayden, et al., "Multiplex-Ready Pcr: A new method for multiplexed SSR and SNP genotyping", BMC Genomics, 9:80:1-12 (2007).
Heid, et al., "Real Time Quantitative PCR", Genome Res., 6:986-94 (1996).
Heilig, et al., "The DNA sequence and analysis of human chromosome 14", Nature, 421:601-09 (2003).
Ho, et al., "Activation Status of T and NK Cells in the Endometrium Throughout Menstrual Cycle and Normal and Abnormal Early Pregnancy", Human Immunology, 49:130-36 (1996).
Hoon, et al., "Detection of Occult Melanoma Cells in Blood With a Multiple-Marker Polymerase Chain Reaction Assay", J. of Clinical Oncology, 13(8):2109-116 (1995).
Hosny, et al., "TP53 mutations in circulating fee DNA from Egyptian patients with non-Hodgkin's lymphoma", Cancer Lett., 275(2):234-39 (2009).
Hsuih, et al., "Novel, ligation-depdent PCR assay for detection of hepatitis C in serum", J. of Clin. Microbiology, 34(3):501-07 (1996).
Huang, et al., "Identification of a family of alternatively splied mRNA species of angiopoietin-1", Blood, 95:1993-99 (2000).
Indolfi, et al., "Perinatal Transmission of Hepatitis C Virus Infection", J. Med. Virol., 81:836- 43 (2009).
International Human Genome Sequencing Consortium, "Initial sequencing and analysis of the human genome", Nature, 409:860-921 (2001).
Irizarry, et al., "Summaries of Affymetrix GeneChip probe level data", Nuc. Acid Res., 31(4):e5 (2003).
Jiang, et al., Noninvasive Fetal Trisomy (NIFTY) test: an advanced noninvasive prenatal diagnosis methodology for fetal autosomal and sex chromosomal aneuploidies. BMC Med Genomics. Dec. 1, 2012;5:57.
Kamnasaran and Cox, "Current status of chromosome 14", J. Med. Genet., 39:81-90 (2002).
Kazakov, et al., "Extracellular DNA in the Blood of Pregnant Women", Tsitologiia (Cytology), 37(3):232-37 (1995).
Kogan, et al., "An improved method for prenatal diagnosis ofgenetic diseases by analysis of amplified DNA sequences", New England J. of Medicine, 317(6):985-90 (1987).
Koumbaris, G. et al. (Jun. 2016, e-published Apr. 26, 2016). "Cell-Free DNA Analysis of Targeted Genomic Regions in Maternal Plasma for Non-Invasive Prenatal Testing of Trisomy 21, Trisomy 18, Trisomy 13, and Fetal Sex," Clin Chem 62(6):848-855.
Krebs, et al., "The Unitarian or Trophoblastic Thesis of Cancer" Medical Record, 163:149-74 (Jul. 1950).
Landegren, et al., "A ligase-mediated gene detection technique", Science, 241:1077 (1988).
Lapair, et al., "Cell-Free DNA in Amniotic Fluid: Unique Fragmentation Signatures in Euploid and Aneuploid Fetuses", Clinical Chem., 53(3):405-11 (2007).
Leon, "Free DNA in the Serum of Cancer Patients and the Effect of Therapy", Cancer Res., 37:646-50 (1977).
Li, et al., "A photocleavable fluorescent nucleotide for DNA sequencing and analysis", PNAS USA, 100(2):414-19 (2003).
Liao, et al., "Targeted massively parallel sequencing of maternal plasma DNA permits efficient and unbiased detection of fetal alleles", Clin Che, 57:92-101 (2011).
Lo, "Fetal nucleic acids in maternal blood: the promises", Clin. Chem. Lab Med., 50(5):xxx-xxx (DOI 10.1515/CCLM.2011.765) (2011).
Lo, et al., "Detection of single-copy fetal DNA sequence from maternal blood", The Lancet, 335:1463-64 (1990).
Lo, et al., "Digital PCR for the molecular detection of fetal chromosomal aneuploidy", PNAS USA, 104:13116-21 (2007).
Lo, et al., Maternal plasma DNA sequencing reveals the genome-wide genetic and mutational profile of the fetus. Sci Transl Med, 2:61ra91 (2010).
Lo, et al., "Plasma placental RNA allelic ratio permits noninvasive prenatal chromosomal aneuploidy detection", Nat. Med., 13:218-23 (2007).
Lo, et al., "Prenatal diagnosis of fetal RhD status by molecular analysis of maternal plasma", N Engl J Med, 339:1734-38 (1998).

(56) References Cited

OTHER PUBLICATIONS

Lo, et al., "Presence of fetal DNA in maternal plasma and serum", The Lancet, 350:485-86 (1997).
Lo, et al., "Quantitative analysis of fetal DNA in maternal plasma and serum: implications for noninvasive prenatal diagnosis", Am J. Hum. Genetics, 62:768-75 (1998).
Lo, et al., "Rapid clearance of fetal DNA from maternal plasma", Am J. Hum. Genetics, 64:218-24 (1999).
Lo, et al., "Two-way cell traffic between mother and fetus: biological and clinical implications", Blood, 88:4390-95 (1996).
Lun, et al., "Microfluidics Digital PCR Reveals a Higher than Expected Fraction of Fetal DNA in Maternal Plasma", Clin. Chem., 54(10):1664-72 (2008).
Lun, et al., "Noninvasive prenatal diagnosis of monogenic diseases by digital size selection and relative mutation dosage on DNA in maternal plasma", PNAS USA, 105(50):19920-25 (2008).
Makrigiorgos, et al., "A PCR-based amplification method retaining the quantitative difference between two complex genomes", Nat. Biotech., 20:936-39 (2002).
Mangs, Curr. Genomics, "The Human Pseudoautosomal Region (PAR): Origin, Function and Future", 8(2):129-36 (2007).
Mansfield, "Diagnosis of Down syndrome and other aneuploidies using quantitative polymerase chain reaction and small tandem repeat polymorphisms", Human Molecular Genetics, 2(1):43-50 (1993).
Mantzaris, et al., "Preliminary report: correct diagnosis of sex in fetal cells isolated from cervical mucus during early pregnancy", ANZJOG, 45(6):529-32 (2005).
Mardis, et al., "The impact of next-generation sequencing technology on genetics", Trends in Genetics, 24(3):133-41 (2007).
Margulies, et al., "Genome sequencing in microfabricated high-density picolitre reactors", Nature, 437(15):376-80 and errata (2005).
Mikhaylov, et al., "Changes in the quantity and synthesis of DNA in the nuclei of large decidual cells of rats in the course of their differentiation", Tsitologia (Cytology), 41(6):677-83 (1992).
Mikhaylov, et al., "Synthesis and content of DNA in human decidual cells at various stages of differentiation according to flow cytometry analysis", Tsitologiia (Cytology), 34(6):67-72 (1992).
Moffet-King, et al., "Natural Killer Cells and Pregnancy", Nature Reviews Immunology, 2002(2):656-63.
Moreno and Gomella, "Circulating Prostate Cancer Cells Detected by Reverse Transcription-Polymerase Chain Reaction (RT-PCR: What do they mean?", Cancer control Journal, 5(6) (1998).
Mueller, et al., "Isolation of fetal trophoblast cells from peripheral blood of pregnant women", The Lancet, 336:197-200 (1990).
Mujezinovic and Alfirevic, Obstet. Gynecol., "Procedure-Related Complications of Amniocentesis and Chorionic Villous Sampling: A Systematic Review", 110(3):687-94 (2007).
Mulcahy, et al., "Plasma DNA K-rase Mutations in Patients with Gastrointestinal Malignancies," Annals New York Academy of Sciences, 25-28.
Myllykangas, S. et al. (2010). "Targeted deep resequencing of the human cancer genome using next-generation technologies," Biotechnol Genet Eng Rev 27:135-158.
Nawroz, et al., "Microsatellite alterations in serum DNA of head and neck cancer patients", Nature Medicine, 2(9):1035-37 (1996).
Nelson, et al., "Alu polymerase chain reaction: A method for rapid isolation of human-specific sequence from complex DNA sources, " PNAS USA, 86:6686-90 (1989).
Ng, et al., "mRNA of placental origin is readily detectable in maternal plasma", PNAS USA, 100:4748-53 (2003).
Nicolaides, et al., "Validation of targeted sequencing of single-nucleotide polymorphisms for non-invasive prenatal detection of aneuploidy of chromosomes 13, 18, 21, X and Y", Prenatal Diagnosis, 33:1-5 (2013).
Oei, et al., "Clusters of regulatory signals for RNA polymerase II transcription associated with Alu family repeats and CpG islands in human promoters", Genomics, 83:873-82 (2004).

Office Action Received on Apr. 11, 2013 for U.S. Appl. No. 13/013,732 (inventor A. Oliphant, filed Jun. 25, 2011), entire document.
Office Action Received on Apr. 14, 2014 for U.S. Appl. No. 13/013,732, filed Jun. 25, 2011, inventor Oliphant, entire document.
Office Action Received on Apr. 15, 2013 for U.S. Appl. No. 13/356,133 (inventor A. Oliphant, filed Jan. 23, 2012), entire document.
Office Action Received on Apr. 5, 2013 for U.S. Appl. No. 13/689,206 (inventor A. Oliphant, filed Nov. 29, 2012), entire document.
Office Action Received on Aug. 30, 2013 for U.S. Appl. No. 13/205,570, filed Aug. 8, 2011, inventor Sparks, entire document.
Office Action Received on Aug. 30, 2013 for U.S. Appl. No. 13/245,133, filed Sep. 26, 2011, inventor Oliphant, entire document.
Office Action Received on Aug. 30, 2013 for U.S. Appl. No. 13/687,169, filed Nov. 28, 2012, inventor Sparks, entire document.
Office Action Received on Aug. 8, 2013 for U.S. Appl. No. 13/605,505, filed Sep. 6, 2012, inventor Struble, entire document.
Office Action Received on Dec. 10, 2013 for U.S. Appl. No. 13/205,490, filed Aug. 8, 2011, inventor Sparks, entire document.
Office Action Received on Dec. 11, 2013 for U.S. Appl. No. 13/274,309, filed Oct. 15, 2011, inventor Struble, entire document.
Office Action Received on Dec. 30, 2013 for U.S. Appl. No. 13/205,603, filed Aug. 8, 2011, inventor Sparks, entire document.
Office Action Received on Dec. 7, 2012 for U.S. Appl. No. 13/013,732 (inventor A. Oliphant, filed Jun. 25, 2011), entire document.
Office Action Received on Feb. 11, 2014 for U.S. Appl. No. 13/689,206, filed Nov. 29, 2012, inventor Oliphant, entire document.
Office Action Received on Feb. 11, 2014 for U.S. Appl. No. 13/405,839, filed Feb. 27, 2012, inventor Oliphant, entire document.
Office Action Received on Feb. 15, 2013 for U.S. Appl. No. 13/689,417 (inventor A. Oliphant, filed Nov. 29, 2012), entire document.
Office Action Received on Feb. 28, 2013 for U.S. Appl. No. 13/205,570 (inventor A. Sparks, filed Aug. 8, 2011), entire document.
Office Action Received on Feb. 28, 2013 for USSN 13/245, 133, filed Sep. 26, 2011, inventor Oliphant, entire document.
Office Action Received on Jan. 31, 2014 for U.S. Appl. No. 13/605,505, filed Sep. 6, 2012, inventor Struble, entire document.
Office Action Received on Jul. 14, 2014 for U.S. Appl. No. 13/293,419, filed Nov. 10, 2011, Sparks, entire document.
Office Action Received on Jul. 16, 2014 for U.S. Appl. No. 13/687,025, filed Nov. 28, 2011, inventor Sparks, entire document.
Office Action Received on Jul. 30, 2014 for U.S. Appl. No. 13/407,978, filed Feb. 29, 2012, inventor Song, entire document.
Office Action Received on Jul. 31, 2013 for U.S. Appl. No. 13/013,732, filed Jun. 25, 2011, inventor Oliphant, entire document.
Office Action Received on Jul. 5, 2012 for U.S. Appl. No. 13/013,732 (inventor A. Oliphant, filed Jun. 25, 2011).
Office Action Received on Jul. 8, 2013 for U.S. Appl. No. 13/205,490, filed Aug. 8, 2011, inventor Sparks (entire document.
Office Action Received on Jun. 13, 2013 for U.S. Appl. No. 13/316,154 (inventor A. Oliphant, filed Dec. 9, 2011), entire document.
Office Action Received on Jun. 13, 2013 for U.S. Appl. No. 13/338,963 (inventor A. Oliphant, filed Dec. 28, 2011), entire document.
Office Action Received on Jun. 25, 2014 for U.S. Appl. No. 13/689,206, filed Nov. 29, 2012, inventor Oliphant, entire document.
Office Action Received on Jun. 26, 2014 for U.S. Appl. No. 13/205,603, filed Aug. 8, 2011, inventor Sparks, entire document.
Office Action Received on Jun. 26, 2014 for U.S. Appl. No. 13/356,133, filed Jan. 23, 2012, inventor Oliphant, entire document.
Office Action Received on Mar. 14, 2013 for U.S. Appl. No. 13/687,025 (inventor A. Sparks, filed Nov. 28, 2012), entire document.
Office Action Received on Mar. 28, 2013 for U.S. Appl. No. 13/687,169 (inventor A. Sparks, filed Nov. 28, 2012), entire document.

(56) References Cited

OTHER PUBLICATIONS

Office Action Received on May 10, 2012 for U.S. Appl. No. 13/293,419 (inventor A. Sparks, filed Nov. 10, 2011), entire document.
Office Action Received on May 12, 2014 for U.S. Appl. No. 13/689,417, filed Nov. 29, 2012, inventor Oliphant, entire document.
Office Action Received on May 13, 2013 for U.S. Appl. No. 13/407,978 (inventor K. Song, filed Feb. 29, 2012), entire document.
Office Action Received on May 17, 2013 for U.S. Appl. No. 13/356,575 (inventor A. Oliphant, filed Jan. 23, 2012), entire document.
Office Action Received on May 8, 2014 for U.S. Appl. No. 13/205,570, filed Aug. 8, 2011, inventor Sparks, entire document.
Office Action Received on May 8, 2014 for U.S. Appl. No. 13/245,133, filed Sep. 26, 2011, inventor Oliphant, entire document.
Office Action Received on May 8, 2014 for U.S. Appl. No. 13/687,169, filed Nov. 28, 2012, inventor Sparks, entire document.
Office Action Received on Oct. 18, 2013 for U.S. Appl. No. 13/356,133, filed Jan. 23, 2012, inventor Oliphant, entire document.
Office Action Received on Oct. 2, 2013 for U.S. Appl. No. 13/687,025, filed Nov. 28, 2012, inventor Sparks, entire document.
Office Action Received on Oct. 25, 2013 for U.S. Appl. No. 13/407,978, filed Feb. 29, 2012, inventor Song, entire document.
Office Action Received on Oct. 31, 2013 for U.S. Appl. No. 13/356,575, filed Jan. 23, 2012, inventor Oliphant, entire document.
Office Action Received on Oct. 31, 2013, filed Dec. 9, 2011, inventor Oliphant for U.S. Appl. No. 13/316,154, entire document.
Page, et al., "Breakpoint diversity illustrates distinct mechanisms for Robertsonian translocation formation", Hum. Molec. Genet., 5(9):1279-88 (1996).
Page, et al., Br. J. Cancer, "Detection of HER2 amplification in circulating free DNA in patients with breast cancer", 104(8):1342-48 (2011).
Palomaki, et al., DNA sequencing of maternal plasma reliably identifies trisomy 18 and trisomy 13 as well as Down syndrome: an international collaborative study. Genet Med. Mar. 2012;14(3):296-305.
Paolella, et al., "The Alu family repeat promoter has a tRNA-like bipartite structure", EMBO J., 2(5):691-96 (1983).
Papageorgiou, et al., "DNA methylation ratio permits noninvasive prenatal diagnosis of trisomy 21", Nat. Med., 17:510-13 (2011).
Petersen, et al., "Down Syndrome Due to De Novo Robertsonian Translocation t(14q21q): DNA Polymorphism Analysis Suggests that the Origin of the Extra q21 is Maternal", Am. JU. Hum. Genet. 49:529-36 (1991).
Poon, et al., "Differential DNA methylation between fetus and mother as a strategy for detecting fetal DNA in maternal plasma", Clin Chem, 48:35-41 (2002).
Porreca, et al., "Multiplex amplification of large sets of human exons", Nat. Methods, 4(11):931-36 (2007).
Rijinders, et al., "Fetal sex determination from maternal plasma in pregnancies at risk for congenital adrenal hyperplasia", Obstet Gynecol, 98:374-78 (2001).
Ro, et al., "Association of Polymorphisms of Interleukin-8, CXCR1, CXCR2, and Selectin With Allograft Outcomes in Kidney Transplantation", Transplantation, 91(1):57-64 (2011).
Robbins, et al., Pathologic Basis of Disease 5th Ed., Chapter 23, pp. 1071-1088 (1994).
Ronaghi, et al., "A Sequencing Method Based on Real_Time Pyrophosphate", Science, 281:363-65 (1998).
Ross, et al., "The DNA sequence of the human X Chromosome", Nature 434:325-37 (2005).
Roth, et al., Molec. Oncol., "Screening for circulating nucleic acids and caspase activity in the peripheral blood as potential diagnostic tools in lung cancer", 5(3):281-91 (2011).
Royston, "An extension of Shapiro and Wilk's W test for normality to large samples", Applied Statistics, 31:115-24 (1982).

Royston, "Model-based screening by risk with application to Down's syndrome", Statistics in Medicine, 11(2)257-68 (1992).
Saiki, et al., "Primer-directed Enzymatic Amplification of DNA with a Thermostable DNA Polymerase", Science, 239:487-91 (1987).
Savas, "Useful genetic variation databases for oncologists investigating the genetic basis of variable treatment response and survival in cancer", Acta Oncol., 49(8):1217-26 (2010).
Schallhammer, et al., "Phenotypic comparison of natural killer cells from peripheral blood and from early pregnancy decidua", Early Pregnancy: Biology and Medicine, 3:15-22 (1997).
Schouten, et al., "Relative quantification of 40 nucleic acid sequences by multiplex ligation-dependent probe amplification", Nuc. Ac. Res., 30(12):e57 (2002).
Schroder, et al., "Transplacental passage of blood cells", J. of Medical Genetics, 12:230-42 (1974).
Schuster, et al., "Next-generation sequencing transforms today's biology", Nat. Methods, 5:16-18 (2008).
Scriven, et al., "Robertsonian translocations—reproductive reisks and indications for preimplantation genetic diagnosis", Human Reproduction, 16(11):2267-73 (2001).
Search Report Received on Apr. 19, 2013 for (PCT/US2012/70177), entire document.
International Search Report mailed on Aug. 12, 2014 for PCT/US2013/075683, filed on Dec. 17, 2013, 5 pages.
Search Report Received on Feb. 21, 2013 for (PCT/US2011/046963), entire document.
Search Report Received on Jan. 20, 2012 for (PCT/US2012/21955).
Search Report Received on May 10, 2012 for (PCT/US2012/026754).
Search Report Received on May 11, 2012 for (PCT/US2012/022261).
Search Report Received on May 14, 2013 for PCT/US2014/17092, entire document.
Search Report Received on May 2, 2012 for PCT/US2011/046935).
Search Report Received on Nov. 15, 2013 for PCT/US2013/51310, entire document.
Search Report Received on Oct. 15, 2012 for (PCT/US2011/046981).
Search Report Received on Sep. 12, 2013 for PCT/US2012/026754, entire document.
Search Report Recevied on Aug. 13, 2012 for (PCT/US2011/046976), entire document.
Sebat, et al., "Strong Association of De Novo Copy Number Mutations with Autism", Science, 316(5823):445-49 (2007).
Sehnert, et al., "Optimal detection of fetal chromosomal abnormalities by massively parallel DNA sequencing of cell-free fetal DNA from maternal blood", Clin Chem, 57: 1042-49 (2011).
Shamash, et al., "Preimplantation genetic haplotyping a new application for diagnosis of translocation carrier's embryo—preliminary observations of two robertsonian translocation carrier families", J. Assist. Reprod. Genet., 28:77-83 (2011).
Shapiro, et al., "Determination of Circulating DNA Levels in Patients with Benign or Malignant Gastrointestinal Disease", Cancer, 51:2116-20 (1983).
Shea, J.L. et al. (Aug. 2013, e-published Feb. 20, 2013). "A new era in prenatal diagnosis: the use of cell-free fetal DNA in maternal circulation for detection of chromosomal aneuploidies," Clin Chem 59(8):1151-1159.
Shen et al. BMC Genetics. 2008. 9:27, 1-18.
Shen et al. "High-throughput SNP genotyping on universal bead arrays," Mutation Research 2005. 573:70-82.
Shendure, et al., "Accurate Multiplex Polony Sequencing of an Evolved Bacterial Genome", Science, 309:1728-32 (2005).
Simpson and Elias, "Isolating Fetal Cells from Maternal Blood", JAMA, 270(19):2357-61 (1993).
Simpson, "Is Cell-Free Fetal DNA from Maternal Blood Finally Ready for Prime Time?", Obst & Gynecol., 119(5):1-3 (2012).
Simpson, et al., "Isolating Fetal Cells in Maternal Circulation for Prenatal Diagnosis", Prenatal Diagnosis, 14:1229-42 (1994).
Smith, et al., "Quantitative phenotyping via deep barcode sequencing", Genome Res., 19:1836-42 (2009).

(56) References Cited

OTHER PUBLICATIONS

Smith, et al., "Detection of melanoma cells in peripheral blood by means of reverse transcriptase and polymerase chain reaction", The Lancet, 338:1227-29 (1991).
Smith, et al.. "Placental apoptosis in normal human pregnancy", Am. J. Obstet. Gynecol, Jul. 1997, pp. 57-65.
Snyder, et al., "Universal noninvasive detection of solid organ transplant rejection", PNAS USA, 108(5):6229-34 (2011).
Sorenson, "Cancer Epidemiology, Biomarkers and Prevention", Cancer Epidem. Biomarkers Prev., 3_67-71 (1994).
Sorenson, et al., "Soluble normal and mutated DNA sequences from single-copy genes in human blood", Cancer Epidemmiol. Biomarkers, 3:64-71 (1994).
Sparks, et al., "Non-invasive prenatal detection and selective analysis of cell-free DNA obtained from maternal blood: evaluation for trisomy 21 and trisomy 18", Am. J. Obstet. Gynecol., (2012), 206:319.e1-9.
Sparks, et al., "Selective analysis of cell-free DNA in maternal blood for evaluation of fetal trisomy", Prenatal Diagnosis, 32:3-9 (2012).
St. Clair, "Copy Number Variation and Schizophrenia", Schizophr. Bull., 35(1):9-12 (2009).
Stroun, et al., "Circulating Nulceic Acids in Higher Organisms", Rev. Cytol. 51:1-48 (1977).
Stroun, et al., "Isolation and Characterization of DNA from the Plasma of Cancer Patients", Eur. J. Cancer Clin. Oncol., 23(6):707-12 (1987).
Stroun, et al., "Neoplastic Characteristics of the DNA Found in the Plasma of Cancer Patients", Oncology, 46:318-322 (1989).
Stroun, et al., The Origin and Mechanism of Circulating DNA, Annals New York Academy of Sciences, 906:161-68 (2000).
Sullivan, et al., "Evidence for Structural Heterogeneity from Molecular Cytogenetic Analysis of Dicentric Robertsonian Translocations", Am. J. Hum. Genet., 59:167-75 (1996).
Tagle, et al., "An optimized Alu-PCR primer pair for human-specific amplification of YACs and somatic cells hybrids", Human Molecular Genetics, 1(2):121-22 (1992).
Tewhey, R. et al. (2009, e-published Nov. 1, 2009). "Microdroplet-based PCR enrichment for large-scale targeted sequencing," Nat Biotechnol 27(11):1025-1031; Supplementary materials: 33 pages.
Tomilin, et al., "Mechanisms of Chromosome Destabilization in Human Cells", Sov. Sci. Rev. D. Physiochem. Biol., 10:39-89 (1992).
Tong, et al., "Noninvasive prenatal detection of fetal trisomy 18 by epigenetic allelic ratio analysis in maternal plasma: theoretical and empirical considerations", Clin Chem, 52:2194-202 (2006).
Tsui, et al., "Noninvasive prenatal diagnosis of hemophilia by microfluidics digital PCR analysis of maternal plasma DNA", Blood, 117:3684-91 (2011).
Tsui, et al., "Systematic microarray-based identification of placental mRNA in maternal plasma: towards noninvasive prenatal gene expression profiling", J. Med Genet, 41:461-67 (2004).
Turner, E.H. et al. (May 2009, e-published Apr. 6, 2009). "Massively parallel exon capture and library-free resequencing across 16 genomes," Nat Methods 6(5):315-316.

U.S. National Library of Medicine. (Jan. 2013). Genetics Home Reference—ATM serine/threonine kinase. Located at <https://ghr.nlm.nih.gov/gene/ATM>, last visited Jun. 13, 2013, 4 pages.
Ulbright, "Germ cell tumors of the gonads: a selective review emphasizing problems in differential diagnosis, newly appreciated, and controversial issues," Modern Pathology, 18:S61-S79 (2005).
Van Opstal, et al., "Rapdi aneuploidy detection with multiplex ligation-dependent probe amplification: a prospective study of 4000 amniotice fluid samples", Eur. J. of Hum. Genetics, 17:112-21 (2009).
Vasioukhin, et al., "Point mutations in the N-ras gene in the blood plasma DNA of patients with myelodysplastic syndrome or acute myelogenous leukaemia", British J. of Haematology, 86:774-79 (1994).
Vogelstein, et al., "Digital PCR", PNAS USA, 96:9236-41 (1999).
Wachtel, et al., "Fetal cells in the maternal circulation: Isolation by multiparameter flow cytometry and confirmation by polymerase chain reaction", Human Reprod., 6(10): 1466-69 (1991).
Wald, et al., "Antenatal maternal serum screening for Down's syndrome: results of a demonstration project", BMJ, 305(6850):391-94 (1992).
Wald, et al., "Maternal serum screening for Down's syndrome in early pregnancy", BMJ, 297:883-87 (1988).
Walker, et al., "Human DNA quantitation using Alu element-based polymerase chain reaction", Analytical Biochem., 315:122-28 (2003).
Wang, et al., "PennCNV: An integrated hidden Markov model designed for high-resolution copy number variation detection in whole-genome SNP genotyping data", Genome Res., 17:1665-74 (2007).
Ward, et al., "Reactivities of serotyping monoclonal antibodies with culture-adapted human rotaviruses", J. Clin. Microbiol. 29(3):422-25 (1991).
Winsor, et al., "Maternal Cell Contamination in Uncultured Amniotic Fluid", Prenatal Diagnosis, 16:49-54 (1996).
Witt, et al., "An improved, non-isotopic method of screening cells from patients with abnormalities of sexual differentiation for Y chromosomal DNA content", J. Med. Genet., 30:304-07 (1993).
Wright, C.F. et al. (Jan.-Feb. 2009, e-published Oct. 22, 2008). "The use of cell-free fetal nucleic acids in maternal blood for non-invasive prenatal diagnosis," Human Reprod Update 15(10):139-151.
Wu and Wallace, "The ligation amplification reaction (LAR)-Amplification of specific DNA sequences using sequential rounds of template-dependent ligation", Genomics, 4:560-69 (1989).
Xie and Tammi, "CNV-seq, a new method to detect copy number variation using high throughput sequencing", BMC Bioinformatics, 10:80 (2008), doi 10.1186/1471-2105-10-80, p. 1-9.
Young and Davis, "Efficient isolation of genes by using antibody probes", PNAS 80:1194-98 (1983).
Zolotukhina, et al., "Analysis of Cell-free DNA in Plasma and Serum of Pregnant Women", J. of Hist. and Cytochem., 53:297-99 (2005).
Mulcahy, et al., "Plasma DNA K-rase Mutations in Patients with Gastrointestinal Malignancies," Annals New York Academy of Sciences, 25-28 Year: 2000.

\* cited by examiner

| Cohort | Status | # subjects | Maternal Age (years) | | | Gestational Age (weeks) | | |
|---|---|---|---|---|---|---|---|---|
| | | | Avg | Min | Max | Avg | Min | Max |
| Training | Disomic | 127 | 34.4 | 18 | 44 | 17.1 | 10.3 | 32.4 |
| | T18 | 8 | 37.7 | 27 | 44 | 18.4 | 13.0 | 25.9 |
| | T21 | 36 | 34.2 | 18 | 44 | 18.9 | 11.0 | 33.0 |
| | Total | 171 | 34.5 | 18 | 44 | 17.6 | 10.3 | 33.0 |
| Validation | Disomic | 123 | 33.1 | 18 | 51 | 18.3 | 11.0 | 30.4 |
| | T18 | 8 | 36.6 | 25 | 43 | 15.7 | 11.7 | 21.0 |
| | T21 | 36 | 34.1 | 18 | 46 | 20.1 | 12.3 | 36.1 |
| | Total | 167 | 33.5 | 18 | 51 | 18.6 | 11.0 | 36.1 |
| Grand Total | | 338 | 34.0 | 18 | 51 | 127 | 18.1 | 10.3 |

Figure 2

RISK CALCULATION FOR EVALUATION OF FETAL ANEUPLOIDY

CROSS-REFERENCE TO RELATED APPLICATIONS

The present application is a continuation of U.S. Ser. No. 16/058,849, filed Aug. 8, 2018; which is a continuation of U.S. Ser. No. 14/853,848, filed Sep. 14, 2015; which is a continuation of U.S. Ser. No. 13/689,417, filed Nov. 29, 2012; which is a continuation of U.S. Ser. No. 13/338,963, filed Dec. 28, 2011; which is a continuation-in-part of U.S. Ser. No. 13/316,154 filed Dec. 9, 2011; which claims priority to U.S. Ser. No. 61/436,135, filed Jan. 25, 2011; all of which are herein incorporated by reference in their entirety.

FIELD OF THE INVENTION

The invention provides a non-invasive method for calculating the risk of fetal genomic copy number variations such as aneuploidies using maternal samples including maternal blood, plasma and serum.

BACKGROUND OF THE INVENTION

In the following discussion certain articles and processes will be described for background and introductory purposes. Nothing contained herein is to be construed as an "admission" of prior art. Applicant expressly reserves the right to demonstrate, where appropriate, that the articles and processes referenced herein do not constitute prior art under the applicable statutory provisions.

The American Congress of Obstetricians and Gynecologists (ACOG) recommends that pregnant women be offered non-invasive screening for fetal chromosomal abnormalities. As such existing screening methods exhibit false positive and negative rates in the range of 5% and 10% respectively, ACOG also recommends that patients categorized by screening as high risk for fetal aneuploidy be offered invasive testing such as amniocentesis or chorionic villus sampling. Although these invasive procedures are highly accurate, they are expensive and entail a risk of loss of normal fetus of approximately 0.5%. To address these limitations, non-invasive methods of fetal aneuploidy detection have been developed.

In particular, more recent attempts to identify aneuploidies have used maternal blood as a starting material. Such efforts have included the use of cell free DNA (cfDNA) to detect fetal aneuploidy in a sample from a pregnant female, including use of massively parallel shotgun sequencing (MPSS) to quantify precisely the increase in cfDNA fragments from trisomic chromosomes. The chromosomal dosage resulting from fetal aneuploidy, however, is directly related to the fraction of fetal cfDNA. Variation of fetal nucleic acid contribution between samples can thus complicate the analysis, as the level of fetal contribution to a maternal sample will vary the amounts needed to be detected for calculating the risk that a fetal chromosome is aneuploid.

For example, a cfDNA sample containing 4% DNA from a fetus with trisomy 21 should exhibit a 2% increase in the proportion of reads from chromosome 21 (chr21) as compared to a normal fetus. Distinguishing a trisomy 21 from a normal fetus with high confidence using a maternal sample with a fetal nucleic acid percentage of 4% requires a large number (>93K) of chromosome 21 observations, which is challenging and not cost-effective using non-selective techniques such as MPSS.

Thus, improved processes for the calculation of the risk of fetal genomic copy number variations, e.g., chromosomal dosage abnormalities such as aneuploidies, would be of great benefit in the art.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

Thus, in one embodiment the present invention provides a computer-implemented process to calculate a risk of fetal aneuploidy in a maternal sample comprising estimating the chromosome dosage for two or more fetal chromosomes in the maternal sample; determining a fetal nucleic acid proportion in the maternal sample; providing data on prior risk of aneuploidy for at least a first fetal chromosome based on extrinsic characteristics; calculating a value of a likelihood that the first fetal chromosome is aneuploid by comparing the chromosome dosage of the first fetal chromosome to the chromosome dosage of a second fetal chromosome in view of the fetal nucleic acid proportion in the maternal sample and the prior risk of aneuploidy; calculating a value of a likelihood that the first fetal chromosome is disomic by comparing the chromosome dosage of the first fetal chromosome to the chromosome dosage of the second fetal chromosome in view of the fetal nucleic acid proportion in the maternal sample and the prior risk of aneuploidy; computing a value of the risk of fetal aneuploiody for the first fetal chromosome based on the value of the likelihood of the chromosome being aneuploid, and the value of the likelihood of the chromosome being disomic.

In some aspects of this embodiment, the maternal sample is a cell free maternal sample, and in some embodiments, the cell free maternal sample is maternal plasma or serum. In yet other aspects, the maternal sample comprises cells.

In some aspects of this embodiment, the data on prior risk of aneuploidy comprises information related to maternal age, and in some aspects, the data on prior risk of aneuploidy comprises information related to gestational age. In yet other embodiments, the data on prior risk of aneuploidy comprises information related to both maternal age and gestational age.

In some aspects of this embodiment, the chromosome dosage of the first and second fetal chromosome is estimated by interrogating one or more loci in the maternal sample on each chromosome for which chromosome dosage is being estimated; in some aspects, the chromosome dosage of the first and second fetal chromosome is estimated by interrogating at least ten loci on each chromosome for which chromosome dosage is being estimated, and in some embodiments, the chromosome dosage of the first and second fetal chromosome is estimated by interrogating at least forty-eight loci or at least ninety-six loci on each chromosome for which chromosome dosage is being estimated.

In some aspects of this embodiment, the loci interrogated for estimation of chromosome dosage of the first and second fetal chromosome are non-polymorphic loci.

In some aspects of this embodiment, determining the fetal nucleic acid proportion in the maternal sample is performed by interrogating one or more polymorphic loci in the maternal sample.

In some aspects of the invention, the risk of fetal aneuploidy is reported as an odds ratio, and in other aspects of the invention, the risk of fetal aneuploidy for the first fetal chromosome is based on a value of a likelihood of the first fetal chromosome being trisomic and a value of the likelihood of the first fetal chromosome being disomic. In other aspects, the risk of fetal aneuploidy for the first fetal chromosome is based on a value of a likelihood of the first fetal chromosome being monosomic and a value of the likelihood of the first fetal chromosome being disomic.

Other embodiments of the invention provide a computer-implemented process to calculate a risk of fetal aneuploidy in a maternal sample comprising estimating the chromosome dosage for two or more fetal chromosomes in the maternal sample; determining a fetal nucleic acid proportion in the maternal sample; calculating a value of a likelihood that a first fetal chromosome is aneuploid by comparing the chromosome dosage of the first fetal chromosome to the chromosome dosage of a second fetal chromosome in view of the fetal nucleic acid proportion in the maternal sample; calculating a value of a likelihood that the first fetal chromosome is disomic by comparing the chromosome dosage of the first fetal chromosome to the chromosome dosage of the second fetal chromosome in view of the fetal nucleic acid proportion in the maternal sample; computing a value of the risk of fetal aneuploiody for the first fetal chromosome based on the value of the likelihood of the chromosome being aneuploid and the value of the likelihood of the chromosome being disomic; providing data on prior risk of aneuploidy for at least the first fetal chromosome based on extrinsic characteristics; and adjusting the value of the risk of fetal aneuploidy based on the data on prior risk of aneuploidy.

In some aspects of this embodiment, the maternal sample is a cell free maternal sample, and in some embodiments, the cell free maternal sample is maternal plasma or serum. In yet other aspects, the maternal sample comprises cells.

In some aspects of this embodiment, the data on prior risk of aneuploidy comprises information related to maternal age, and in some aspects, the data on prior risk of aneuploidy comprises information related to gestational age. In yet other embodiments, the data on prior risk of aneuploidy comprises information related to both maternal age and gestational age.

In some aspects of this embodiment, the chromosome dosage of the first and second fetal chromosome is estimated by interrogating one or more loci in the maternal sample on each chromosome for which chromosome dosage is being estimated; in some aspects, the chromosome dosage of the first and second fetal chromosome is estimated by interrogating at least ten loci on each chromosome for which chromosome dosage is being estimated, and in some embodiments, the chromosome dosage of the first and second fetal chromosome is estimated by interrogating at least forty-eight loci or at least ninety-six loci on each chromosome for which chromosome dosage is being estimated.

In some aspects of this embodiment, the loci interrogated for estimation of chromosome dosage of the first and second fetal chromosome are non-polymorphic loci.

In some aspects of this embodiment, determining the fetal nucleic acid proportion in the maternal sample is performed by interrogating one or more polymorphic loci in the maternal sample.

In some aspects of the invention, the risk of fetal aneuploidy is reported as an odds ratio, and in other aspects of the invention, the risk of fetal aneuploidy for the first fetal chromosome is based on a value of a likelihood of the first fetal chromosome being trisomic and a value of the likelihood of the first fetal chromosome being disomic. In other aspects, the risk of fetal aneuploidy for the first fetal chromosome is based on a value of a likelihood of the first fetal chromosome being monosomic and a value of the likelihood of the first fetal chromosome being disomic.

Numerous ways of determining the fetal nucleic acid proportion can be used, as described in more detail herein. In certain aspects, the fetal nucleic acid proportion is determined for a single fetal chromosome. In other aspects, the fetal nucleic acid proportion is determined for two or more fetal chromosomes. In yet other aspects, the fetal nucleic acid proportion reflects the total proportion of fetal nucleic acids in the maternal sample.

DESCRIPTION OF THE FIGURES

FIG. 2 is a table with demographics of the subjects from which maternal samples were obtained and analyzed in the Examples.

DETAILED DESCRIPTION OF THE INVENTION

Figure 1:
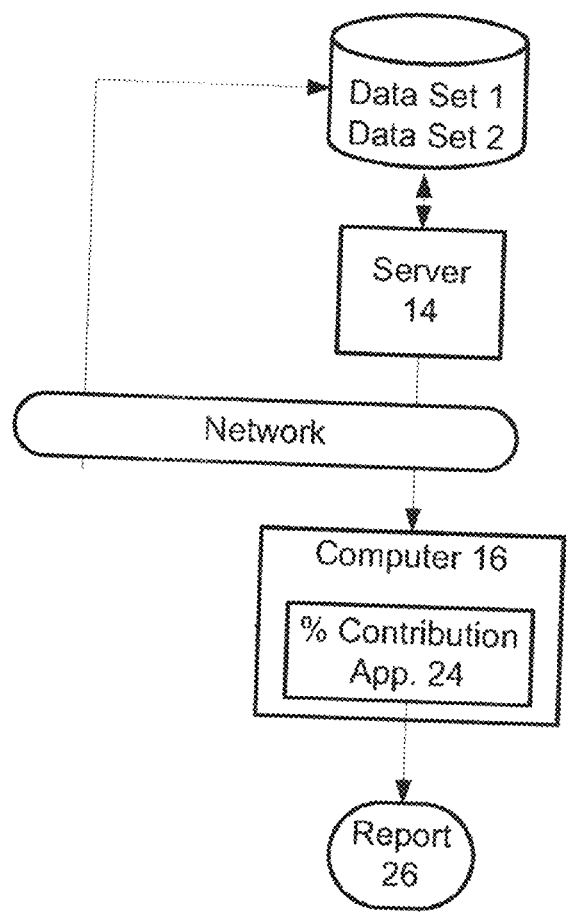
FIG. 1 is a block diagram illustrating an exemplary system environment.

The processes described herein may employ, unless otherwise indicated, conventional techniques and descriptions of molecular biology (including recombinant techniques), genomics, biochemistry, and sequencing technology, which are within the skill of those who practice in the art. Such conventional techniques include hybridization and ligation of oligonucleotides, next generation sequencing, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, et al., Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Stryer, L., *Biochemistry* (4$^{th}$ Ed.) W.H. Freeman, New York (1995); Gait, "*Oligonucleotide Synthesis: A Practical Approach*" IRL Press, London (1984); Nelson and Cox, Lehninger, *Principles of Biochemistry*, 3$^{rd}$ Ed., W. H. Freeman Pub., New York (2000); and Berg et al., *Biochemistry*, 5$^{th}$ Ed., W.H. Freeman Pub., New York (2002), all of which are herein incorporated by reference in their entirety for all purposes. Before the present compositions, research tools and processes are described, it is to be understood that this invention is not limited to the specific processes, compositions, targets and uses described, as such may, of course, vary. It is also to be understood that the terminology used herein is for the purpose of describing particular aspects only and is not intended to limit the scope of the present invention, which will be limited only by appended claims.

It should be noted that as used herein and in the appended claims, the singular forms "a," "and," and "the" include plural referents unless the context clearly dictates otherwise. Thus, for example, reference to "a nucleic acid region" refers to one, more than one, or mixtures of such regions, and reference to "an assay" includes reference to equivalent steps and processes known to those skilled in the art, and so forth.

Where a range of values is provided, it is to be understood that each intervening value between the upper and lower limit of that range—and any other stated or intervening value in that stated range—is encompassed within the invention. Where the stated range includes upper and lower limits, ranges excluding either of those included limits are also included in the invention.

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated. All publications mentioned herein, and in particular patent applications and issued patents, are incorporated by reference for the purpose of describing and disclosing various aspects, details and uses of the processes and systems that are described in the publication and which might be used in connection with the presently described invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Definitions

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "amplified nucleic acid" is any nucleic acid molecule whose amount has been increased at least two fold by any nucleic acid amplification or replication process performed in vitro as compared to the starting amount in a maternal sample.

The term "chromosomal dosage abnormality" refers to duplications or deletions of all (aneuploidy) or part of a chromosome.

The term "diagnostic tool" as used herein refers to any composition or assay of the invention used in combination as, for example, in a system in order to carry out a diagnostic test or assay on a patient sample.

The term "distinguishing region" refers to a region that is measurably different between loci. Such differences include, but are not limited to, single nucleotide polymorphisms (SNPs), differences in methylation status, mutations including point mutations and indels, short tandem repeats, copy number variants, and the like.

The term "hybridization" generally means the reaction by which the pairing of complementary strands of nucleic acid occurs. DNA is usually double-stranded, and when the strands are separated they will re-hybridize under the appropriate conditions. Hybrids can form between DNA-DNA, DNA-RNA or RNA-RNA. They can form between a short strand and a long strand containing a region complementary to the short one. Imperfect hybrids can also form, but the more imperfect they are, the less stable they will be (and the less likely to form).

The term "extrinsic factor" includes any information pertinent to the calculation of an odds ratio that is not empirically derived through detection of a maternal and fetal locus. Examples of such extrinsic factors include information related to maternal age, information related to gestational age, information related to previous pregnancies with an aneuploid fetus, previous serum screening results and the like. In preferred embodiments, the step of adjusting the computed odds ratio uses extrinsic factors related to both maternal age and gestational age.

The terms "locus" and "loci" as used herein refer to a nucleic acid region of known location in a genome.

The term "informative locus" as used herein refers to a locus with one or more distinguishing regions which is homozygous in one source and heterozygous in another source within a mixed sample.

The term "maternal sample" as used herein refers to any sample taken from a pregnant mammal which comprises a maternal source and a fetal source of nucleic acids (e.g., RNA or DNA).

As used herein "polymerase chain reaction" or "PCR" refers to a technique for replicating a specific piece of target DNA in vitro, even in the presence of excess non-specific DNA. Primers are added to the target DNA, where the primers initiate the copying of the target DNA using nucleotides and, typically, Taq polymerase or the like. By cycling the temperature, the target DNA is repetitively denatured and copied. A single copy of the target DNA, even if mixed in with other, random DNA, can be amplified to obtain billions of replicates. The polymerase chain reaction can be used to detect and measure very small amounts of DNA and to create customized pieces of DNA. In some instances, linear amplification processes may be used as an alternative to PCR.

The term "polymorphism" as used herein refers to any genetic characteristic in a locus that may be indicative of that particular locus, including but not limited to single nucleotide polymorphisms (SNPs), methylation differences, short tandem repeats (STRs), and the like.

Generally, a "primer" is an oligonucleotide used to, e.g., prime DNA extension, ligation and/or synthesis, such as in the synthesis step of the polymerase chain reaction or in the primer extension techniques used in certain sequencing reactions. A primer may also be used in hybridization techniques as a means to provide complementarity of a nucleic acid region to a capture oligonucleotide for detection of a specific nucleic acid region.

The term "research tool" as used herein refers to any composition or assay of the invention used for scientific enquiry, academic or commercial in nature, including the development of pharmaceutical and/or biological therapeutics. The research tools of the invention are not intended to be therapeutic or to be subject to regulatory approval; rather, the research tools of the invention are intended to facilitate research and aid in such development activities, including any activities performed with the intention to produce information to support a regulatory submission.

The term "selected nucleic acid region" as used herein refers to a nucleic acid region corresponding to a genomic region on an individual chromosome. Such selected nucleic acid regions may be directly isolated and enriched from the sample for detection, e.g., based on hybridization and/or other sequence-based techniques, or they may be amplified using the sample as a template prior to detection of the sequence. Nucleic acids regions for use in the processing systems of the present invention may be selected on the basis of DNA level variation between individuals, based upon specificity for a particular chromosome, based on CG content and/or required amplification conditions of the selected nucleic acid regions, or other characteristics that will be apparent to one skilled in the art upon reading the present disclosure.

The terms "sequencing", "sequence determination" and the like as used herein refers generally to any and all biochemical processes that may be used to determine the order of nucleotide bases in a nucleic acid.

The term "specifically binds", "specific binding" and the like as used herein, refers to one or more molecules (e.g., a nucleic acid probe or primer, antibody, etc.) that binds to another molecule, resulting in the generation of a statistically significant positive signal under designated assay conditions. Typically the interaction will subsequently result in a detectable signal that is at least twice the standard deviation of any signal generated as a result of undesired interactions (background).

The term "value of the likelihood" refers to any value achieved by directly calculating likelihood or any value that can be correlated to or otherwise indicative of a likelihood.

The term "value of the probability" refers to any value achieved by directly calculating probability or any value that can be correlated to or otherwise indicative of a probability.

The Invention in General

Chromosomal dosage resulting from fetal aneuploidy can be detected using nucleic acids from a maternal sample. In addition to empirical determination of the frequency of nucleic acids from a particular chromosome, the proportion of fetal nucleic acids in the maternal sample is also useful in determining the risk of fetal aneuploidy based on chromosome dosage, as it will impact the level of variation that is statistically significant in terms of the risk calculation. Utilizing such information in calculating the risk of an aneuploidy in one or more fetal chromosomes allows for a more accurate result that reflects the biological differences between samples.

Determination of Fetal DNA Proportion in a Maternal Sample

The proportion of fetal DNA in a maternal sample is used as a part of the risk calculation of the present invention, as fetal proportion provides important information on the expected statistical presence of chromosomal dosage. Variation from the expected statistical presence may be indicative of fetal aneuploidy, an in particular a fetal trisomy or monosomy of a particular chromosome.

Any methods known in the art to estimate the percentage of fetal DNA in a maternal sample may be used, some of which are described below. Using fetal proportion as one component of the risk calculation is particularly helpful in circumstances where the level of fetal DNA in a maternal sample is low. Further, knowledge of the fetal DNA percentage may be used to determine what if any additional analyses can be performed on the sample, as it may be the case at a certain lower bound of fetal DNA percentage a system is not able to reliably perform analysis. In other aspects, determining the fetal DNA proportion in a maternal sample may additionally affect the level of certainty or power in detecting a fetal aneuploidy.

Although the following methods are described for determination of a total proportion of fetal content in a maternal sample, the proportion can also be determined on a chromosome by chromosome basis. For instance frequency information for fetal chromosome 21 can be determined as compared to fetal chromosome 18. In another example, two or more chromosomes can be used in detecting a fetal proportion, e.g., frequency of loci on chromosomes 1 and 2 can be used. In certain aspects, the chromosome used for determining fetal proportion is the chromosome interrogated for possible aneuploidy. In another aspect, the chromosome(s) used for determining fetal proportion are specifically not the chromosome interrogated for possible aneuploidy.

Determination of Fetal DNA Content in a Maternal Sample Using Y-specific Sequences.

In circumstances where the fetus is male, percent fetal DNA in a sample can be determined through detection of Y-specific nucleic acids and compared to maternal DNA content. For example, quantities of an amplified Y-specific nucleic acid such as a region from the sex-determining region Y gene (SRY), which is located on the Y chromosome and thus representative of fetal DNA in this circumstance, can be determined and compared to one or more amplified genomic regions that are present in both maternal DNA and fetal DNA (genomic regions that preferably are not from a chromosome believed to potentially be aneuploid in the fetus, e.g., an autosomal region that is not on chromosome 21, 18, or 13).

In another example, the fetal DNA concentration in a sample is calculated using methods that take into account the small percentage of background maternal DNA that may be incorrectly identified as originating from chromosome Y. Specifically, using certain bioinformatics algorithms, a small number of DNA molecules are incorrectly identified as originating from chromosome Y in pregnancies with female fetuses (see, Chiu, et al., PNAS USA, 105:20458-63 (2008)). The % chrY value in a pregnancy with a male fetus is thus a composite of the amount of chromosome Y sequences contributed by the male fetus and those sequences from the maternal background DNA that are incorrectly assigned to chromosome Y. Accordingly, in certain aspects, the fetal DNA concentration can be more correctly derived from the equation: chrY %=0.157F+0.007(1−F) (see, Chiu, et al., BMJ, 342:c7401 (2011)).

In a preferred aspect, amplified DNA from cell free DNA is produced by the polymerase chain reaction (PCR). Other mechanisms for amplification can be used as well as will be apparent to one skilled in the art upon reading the present disclosure, including those described in more detail herein. In particular aspects, the percentage of cell free fetal DNA in the maternal sample can be determined by PCR using serially-diluted DNA isolated from the maternal sample, which can accurately quantify the number of genomes comprising the amplified genes. For example, if a blood sample contains 100% male fetal DNA, and 1:2 serial dilutions are performed, then on average the SRY signal will disappear 1 dilution before an autosomal signal, since there is 1 copy of the SRY gene and 2 copies of an autosomal gene.

In a specific aspect, the percentage of cell free fetal DNA in maternal plasma is calculated using the following formula: percentage of cell free fetal DNA=(No. of copies of SRY gene×2×100)/(No. of copies of autosomal gene), where the number of copies of each gene is determined by observing the highest serial dilution in which the gene was detected. The formula contains a multiplication factor of 2, which is used to normalize for the fact that there is only 1 copy of the SRY gene compared to two copies of the autosomal gene in each genome, fetal or maternal.

Determination of Fetal DNA Content in a Maternal Sample Using Autosomal Informative Loci.

The DNA from a fetus will have approximately 50% of its loci inherited from the mother and approximately 50% its loci inherited from the father. Determining which genetic loci are contributed to the fetus from non-maternal sources (informative loci) allows the estimation of fetal DNA proportion in a maternal sample, and thus provides information used to calculate statistically significant differences in chromosomal dosages for chromosomes of interest.

In certain aspects, determination of fetal polymorphisms requires targeted SNP and/or mutation analysis to identify the presence of fetal DNA in a maternal sample. In some aspects, prior genotyping of the father and/or mother may be used. For example, the parents may have undergone genotype determination to identify disease markers, e.g., markers for disorders such as cystic fibrosis, muscular dystrophy, spinal muscular atrophy or even the status of the RhD gene. Differences in polymorphisms, copy number variants or mutations can be used to determine the percentage fetal contribution in a maternal sample.

In one preferred aspect, the percent fetal cell free DNA in a maternal sample can be quantified using multiplexed SNP detection without prior knowledge of the maternal or paternal genotype. In this aspect, two or more selected polymorphic nucleic acid regions with a known SNP in each region are used. In a preferred aspect, the selected polymorphic nucleic acid regions are located on an autosomal chromosome that is unlikely to be aneuploid, e.g., not chromosomes 21, 18, or 13. The selected polymorphic nucleic acid regions from the maternal sample (e.g., plasma) are amplified. In a preferred aspect, the amplification is universal; and in a preferred embodiment, the selected polymorphic nucleic acid regions are amplified in one reaction in one vessel. Each allele of the selected polymorphic nucleic acid regions in the maternal sample is determined and quantified. In a preferred aspect, high throughput sequencing is used for such determination and quantification.

Loci are thus identified where the maternal and fetal genotypes are different; e.g., the maternal genotype is homozygous and the fetal genotype is heterozygous. This identification of informative loci is accomplished by observing a high frequency of one allele (>80%) and a low frequency (<20% and >0.15%) of the other allele for a particular selected nucleic acid region. The use of multiple loci is particularly advantageous as it reduces the amount of variation in the measurement of the abundance of the alleles between loci. All or a subset of the loci that meet this requirement are used to determine fetal contribution through statistical analysis. In one aspect, fetal contribution is determined by summing the low frequency alleles from two or more loci together, dividing by the sum of the low and high frequency alleles and multiplying by two.

For many alleles, maternal and fetal sequences may be homozygous and identical, and as this information therefore does not distinguish between maternal and fetal DNA it is not useful in the determination of percent fetal DNA in a maternal sample. The present invention utilizes allelic information where there is a distinguishable difference between the fetal and maternal DNA (e.g., a fetal allele containing at least one allele that differs from the maternal allele) in calculations of percent fetal DNA. Data pertaining to allelic regions that are the same for maternal and fetal DNA are thus not selected for analysis, or are removed from the pertinent data prior to determination of the fetal DNA proportion so as not to mask the useful data. Additional exemplary processes for quantifying fetal DNA in maternal plasma can be found, e.g., in Chu, et al., Prenat. Diagn., 30:1226-29 (2010), which is incorporated herein by reference.

In one aspect, data from selected nucleic acid regions may be excluded if the data from the region appears to be an outlier due to experimental error or from idiopathic genetic bias within a particular sample. In another aspect, selected data from certain nucleic acid regions may undergo statistical or mathematical adjustment such as normalization, standardization, clustering, or transformation prior to summation or averaging. In another aspect, data from selected nucleic acid regions may undergo both normalization and data experimental error exclusion prior to summation or averaging.

In a preferred aspect, data from 12 or more nucleic acid regions or loci are used for the analysis. In another preferred aspect, data from 24 or more nucleic acid regions or loci are used for the analysis. In another preferred aspect, data from 48 or more loci are used for the analysis. In another aspect, one or more indices are used to identify the sample, the locus, the allele or the identification of the nucleic acid. Such indices are as is described in co-pending application Ser. Nos. 13/205,490 and 13/205,570 hereby incorporated herein by reference in their entirety.

In one preferred aspect, the percentage fetal contribution in a maternal sample is quantified using tandem SNP detection in the maternal and fetal alleles. Techniques for identifying tandem SNPs in DNA extracted from a maternal sample are disclosed in Mitchell et al, U.S. Pat. No. 7,799, 531 and U.S. patent application Ser. Nos. 12/581,070, 12/581,083, 12/689,924, and 12/850,588. These references describe the differentiation of fetal and maternal loci through detection of at least one tandem single nucleotide polymorphism (SNP) in a maternal sample that has a different haplotype between the fetal and maternal genome. Identification and quantification of these haplotypes can be performed directly on the maternal sample and used to determine the fetal proportion of nucleic acids in the maternal sample.

Determination of Fetal DNA Content in a Maternal Sample Using Epigenetic Allelic Ratios Certain genes have been identified as having epigenetic differences between the fetus and the mother, and such genes are candidate loci for fetal DNA markers in a maternal sample. See, e.g., Chim, et al., PNAS USA, 102:14753-58 (2005). These loci, which are unmethylated in the fetus but are methylated in maternal blood cells, can be readily detected in maternal plasma. The comparison of methylated and unmethylated amplification products from a maternal sample can be used to quantify the percent fetal DNA contribution to the maternal sample by calculating the epigenetic allelic ratio for one or more of such sequences known to be differentially-methylated in fetal DNA as compared to maternal DNA.

To determine methylation status of nucleic acids in a maternal sample, the nucleic acids of the sample are subjected to bisulfite conversion. Conventional processes for such bisulphite conversion include, but are not limited to, use of commercially available kits such as the Methylamp™ DNA Modification Kit (Epigentek, Brooklyn, NY). Allelic frequencies and ratios can be directly calculated and exported from the data to determine the percentage of fetal DNA in the maternal sample.

Empirical Estimation of Chromosome Dosage

The dosage of fetal chromosomes used in the odds risk calculation can be estimated using a variety of techniques. The processes for detection include polymorphic detection, such as SNP detection of specific nucleic acids, or preferably non-polymorphic detection based on fetal and maternal sequences, and preferably conserved non-polymorphic sequences between the mother and fetus. These detection methods can determine both dosage of a particular chromosome, as well as the overall proportion of fetal nucleic acids in a maternal sample relative to the maternal contribution.

In estimating chromosome dosage, such frequency measurements are preferably total frequencies of the selected nucleic acid in the sample regardless of the source, and thus it is not required that the selected nucleic acids be distinguished as being from a maternal or fetal source prior to the use in the odds risk calculation.

In some aspects, nucleic acids can be selected from a maternal sample prior to detection, i.e. selectively isolated from a maternal sample prior to detection using amplification or capture techniques such as hybridization. In another specific aspect, the nucleic acids used in estimation of chromosome dosage may be selected after detection, e.g., by filtering frequency data generated from techniques such as massively parallel shotgun sequencing of nucleic acids within the maternal sample.

In some specific aspects, estimation of chromosome dosage employs selective sequencing methods that interrogate chromosome-specific loci, enabling highly multiplexed sequencing of selected loci from specific chromosomes of interest. Chromosome-selective sequencing can be used to assay simultaneously polymorphic and non-polymorphic loci in a single reaction, enabling estimation of both chromosome dosage and fetal proportion of fetal nucleic acids in the maternal sample. Subsequently, a novel risk calculation of the invention can employed, which leverages chromosome dosage and fetal proportion estimates to compute the likelihood of fetal aneuploidy (e.g., fetal trisomy) in each subject.

In one aspect, the present invention utilizes analysis of random DNA segments, such as that described in, e.g., Quake et al., U.S. Pat. Nos. 8,008,018 and 7,888,017, and Shoemaker et al., to estimate chromosome dosage (aneuploidy). Briefly, the quantity of nucleic acids within a mixed sample such as a maternal sample can be differentially detected using selected nucleic acid sequences. The nucleic acids may be genomic DNA or RNA, and preferably are mRNA. In the case of mRNA, one may choose target sequences corresponding to genes that are highly expressed in the fetus. The nucleic acids in each sample are detected with one or more sequence-specific probes directed to at least one of two target sequences in the nucleic acids to obtain a detectible reaction product. A probe specific to an interrogated chromosome is combined with the reaction sample, along with a control probe specific to another (e.g., non-interrogated) chromosome. In most cases, the reaction products will be from maternal nucleic acids, but a small number of reaction products will be from fetal nucleic acids. In order to distinguish random variation from fetal results, a large number of reactions are run, and statistical processes are applied to the results. Labeling and detection in the present process is used to distinguish the presence or absence of a single target sequence, referred to as "digital analysis," although it may be performed with sensitive nucleic acid detection processes that distinguish between one and more than one target sequence in a discrete sample.

In another example, massively parallel sequencing of nucleic acids (e.g., DNA fragments randomly selected from the sample) is used to determine the sequence of the nucleic acids in the maternal sample to determine selected frequency of the nucleic acids within the maternal sample. For detection of a chromosome frequency abnormality (e.g., a trisomy), the sequenced nucleic acids are identified as being from a first chromosome, and the total amounts of nucleic acids from at least one first chromosome in the maternal sample are compared to total amounts of nucleic acids from at least one second chromosome in the maternal sample. The total nucleic acid amounts include the nucleic acids from both the fetus and mother in the maternal sample, and the nucleic acids from the fetus are not differentiated from the maternal in determining the frequency of the nucleic acids corresponding to the chromosome frequency. Where one first chromosome is presumed to be euploid, and the second chromosome is suspected to be aneuploid, the total numbers of nucleic acids for the first and second chromosomes are compared to determine the presence or absence of said aneuploidy.

In more specific aspects, the samples used for massively parallel sequencing of nucleic acids are enriched for polymorphic regions. Exemplary techniques for performing enrichment include those disclosed in, e.g., WO2011091063, WO2011091046 and US Pat Appln No. 20110230358. Briefly, a portion of a maternal sample comprising cell free DNA is amplified to augment the number of copies of the one or more polymorphic sequences in the sample, and the amplified portions of nucleic acids are then added back to the original sample for sequencing. Alternatively, the sample is subjected to whole genome sequencing to obtain a plurality of sequence tags, and the sequences of the tags are compared to the sequence of multiple reference polymorphisms.

In some aspects, the nucleic acids are sequenced using array-based hybridization processes, such as those described in U.S. Pat. Pub. No. 2011/0172111. In other aspects, the biomolecules are detected using nanopore technology detection, such as those described in U.S. Pat. Pub. No. 2011/0124518.

In another aspect, the nucleic acids are sequenced and compared using polymorphisms that differentiate between maternal and fetal alleles in a sample, using methods such as those described in U.S. Pat. Nos. 7,727,720, 7,718,370, 7,598,060, 7,442,506, 7,332,277, 7,208, 274, and 6,977,162. Briefly, the methods utilize polymorphic detection to identify chromosomal abnormalities. Sequences are determined at alleles that are homozygous in the mother and heterozygous in the fetus, and a ratio for the heterozygous alleles is determined. The ratio for the heterozygous alleles is used to indicate the presence or absence of a chromosomal abnormality.

In yet another aspect, estimation of the risk of fetal aneuploidies utilizes identification of tandem polymorphisms, such as that described in, e.g., U.S. Pat. No. 7,799, 531, and U.S. Pub. Nos. 2011/0117548, 2011/0059451, 2010/0184044, 2010/184043, and 2008/0020390. Briefly, tandem SNPs are detected and used to differentiate maternal and fetal alleles in a maternal sample to detect fetal chromosomal abnormalities through comparison of maternal DNA to fetal DNA.

In a preferred aspect, the estimation of chromosomal dosage utilizes selected amplification of representative loci. Such techniques are disclosed in, e.g., U.S. application Ser. Nos. 13/013,732, 13/205,490, 13/205,570, and 13/205,603, all of which are incorporated herein in their entirety. These techniques utilize detection of genomic regions using fixed sequence oligonucleotides and joining the fixed sequence oligonucleotides via ligation and/or extension. This can be accomplished using a combination of ligation and amplification, e.g., the ligation of two or more fixed sequence oligonucleotides and optionally a bridging oligonucleotide that is complementary to a region between the fixed sequence oligonucleotides. In another example, this can be accomplished using a combination of extension, ligation and amplification.

In some aspects, chromosomal dosage estimations and variations for the normal population are determined from normal samples that have a similar proportion of fetal DNA. For example, an expected chromosomal dosage for trisomy in a DNA sample with a specific percent fetal cell free DNA can be calculated by adding the percent contribution from the aneuploid chromosome. The chromosomal dosage for the sample may then be compared to the chromosomal dosage for a normal fetus and to an expected chromosomal dosage if triploid to determine statistically, using the variation of the chromosomal dosage, if the sample is more likely normal or triploid, and the statistical probability that it is one or the other.

In a preferred aspect, the nucleic acid regions selected for analysis in the maternal sample include in a single reaction both nucleic acid regions for determination of percent fetal contribution as well as nucleic acid regions corresponding to two or more chromosomes used to detect a chromosomal dosage abnormality. The use of a single reaction helps to minimize the risk of contamination or bias that may be introduced using separate reactions, which may otherwise skew results. In fact, the methods of the present invention are preferably performed as multiplexed or even highly-multiplexed reactions, where both polymorphic and non-polymorphic loci (for determining percent fetal contribution and chromosome dosage, respectively) are interrogated in a single reaction for each sample. In preferred embodiments, the multiplexing assays described in U.S. application Ser. Nos. 13/013,732, 13/205,490, 13/205,570, and 13/205,603 are used, as these assays query both polymorphic and non-polymorphic loci in a maternal sample in a single multiplexed reaction.

In other aspects, one or more selected nucleic acid regions may be interrogated both for determination of fetal nucleic acid proportion as well as detection of fetal aneuploidies. Utilizing the same regions for both fetal percent contribution and detection of fetal aneuploidies further aids in minimizing bias due to experimental error or contamination.

Computer implementation of the Processes of the Invention

FIG. 1 is a block diagram illustrating an exemplary system environment in which the processes of the present invention may be implemented for calculating the relevant values. The system 10 includes a server 14 and a computer 16. The computer 16 may be in communication with the server 14 through the same or different network.

According to the exemplary embodiment, the computer 16 executes a software component 24 that calculates fetal proportion and applies this information to the values of the dosage of genomic regions and/or chromosomes. In one embodiment, the computer 16 may comprise a personal computer, but the computer 16 may comprise any type of machine that includes at least one processor and memory.

The output of the software component 24 comprises a report 26 with a value of probability that a genomic region and/or a chromosome has a dosage abnormality. In a preferred aspect this report is an odds ratio of a value of the likelihood that a region or chromosome has two copies (e.g., is disomic) and a value of the likelihood that a region or chromosome has more copies (e.g., is trisomic) or less copies (e.g., is monosomic) copies. The report 26 may be paper that is printed out, or electronic, which may be displayed on a monitor and/or communicated electronically to users via e-mail, FTP, text messaging, posted on a server, and the like.

Although the normalization process of the invention is shown as being implemented as software 24, it can also be implemented as a combination of hardware and software. In addition, the software 24 for normalization may be implemented as multiple components operating on the same or different computers.

Both the server 14 and the computer 16 may include hardware components of typical computing devices (not shown), including a processor, input devices (e.g., keyboard, pointing device, microphone for voice commands, buttons, touchscreen, etc.), and output devices (e.g., a display device, speakers, and the like). The server 14 and computer 16 may include computer-readable media, e.g., memory and storage devices (e.g., flash memory, hard drive, optical disk drive, magnetic disk drive, and the like) containing computer instructions that implement the functionality disclosed when executed by the processor. The server 14 and the computer 16 may further include wired or wireless network communication interfaces for communication.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

The efficiency and accuracy of identifying aneuploidies using the odds ratio calculation of the present invention is demonstrated in the below Examples, where in a blinded cohort of 167 pregnant women, including 36 T21 and 8 T18 pregnancies, the methods correctly discriminated all T21 and T18 cases from euploid cases.

Example 1: Subjects

Subjects were prospectively enrolled upon providing informed consent under protocols approved by institutional review boards. Subjects were required to be at least 18 years of age, at least 10 weeks gestational age, and to have singleton pregnancies. A subset of enrolled subjects, consisting of 250 women with disomic pregnancies, 72 women with trisomy 21 (T21) pregnancies, and 16 women with trisomy 18 (T18) pregnancies, was selected for inclusion in this study. The subjects were randomized into a first cohort consisting of 127 disomic pregnancies, 36 T21 pregnancies, and 8 T18 pregnancies, and a second cohort consisting of 123 disomic pregnancies, 36 T21 pregnancies, and 8 T18 pregnancies. The trisomy status of each pregnancy was confirmed by invasive testing (fluorescent in-situ hybridization and/or karyotype analysis). The trisomy status of the first cohort was known at the time of analysis; in the second cohort, trisomy status was blinded until after risk calculation analysis.

FIG. 2 is a table profiling the demographics of the samples analyzed in this study. The mean maternal age of the disomic, T21, and T18 subjects was 34, 34, and 37 years, respectively. The mean gestational age of the disomic, T21, and T18 subjects was 17.7, 19.6, and 17.0 weeks. The mean maternal ages of the disomic, T21 and T18 subjects were not significantly different between the first versus second cohorts (all T-test p>0.05). Similarly, the mean gestational ages of the disomic, T21 and T18 subjects were not significantly different between the first versus second cohorts (all T-test p>0.05).

Example 2: Analysis of Non-Polymorphic Loci to Estimate Chromosome Dosage

To estimate fetal chromosome dosage, assays were designed against 576 non-polymorphic loci on each of chromosome 18 and 21, where each assay consisted of three locus-specific oligonucleotides: a left oligo with a 5' universal amplification tail, a 5' phosphorylated middle oligo, and a 5' phosphorylated right oligo with a 3' universal amplification tail. The selected loci were used to compute a chr21 dosage metric and a chr18 dosage metric for each sample. First cohort samples were analyzed to identify 384 of the 576 loci on chr21 and chr18 best able to discriminate T21 and T18 from normal samples. First, sequence counts were normalized by systematically removing sample and assay biases using median polish (see Tukey, *Exploratory Data Analysis* (Addison-Wesley, Reading MA, 1977) and Irzarry, et al., NAR, 31(4):e15 (2003)).

Next, the 384 loci on each chromosome exhibiting the greatest residual difference between normal and trisomy samples were identified using Z Statistics derived from individual loci for the test chromosome and all 576 loci for the comparison chromosome. The mean of counts from the 384 chr21 loci best able to discriminate T21 from normal were divided by the sum of the mean count for the 384 chr21 and mean count for all 576 chr18 loci. A chr18 proportion metric was calculated similarly as the sum of counts from the 384 chr18 loci best able to discriminate T18 from normal divided by the sum of the mean count from all 576 chr21 loci and the mean count for the 384 chr18 loci.

A standard Z test of proportions was used to compute Z statistics:

$$Z_j = \frac{p_j - p_0}{\sqrt{\frac{p_j(1-p_j)}{n_j}}}$$

where $p_j$ is the observed proportion for a given chromosome of interest in a given sample j, $p_o$ is the expected proportion for the given test chromosome calculated as the median $p_j$, and $n_j$ is the denominator of the proportion metric. Z statistic standardization was performed using iterative censoring. At each iteration, the samples falling outside of three median absolute deviations were removed. After ten iterations, mean and standard deviation were calculated using only the uncensored samples. All samples were then standardized against this mean and standard deviation. The Kolmogorov-Smirnov test (see Conover, *Practical Nonparametric Statistics*, pp. 295-301 (John Wiley & Sons, New York, NY, 1971)) and Shapiro-Wilk's test (see Royston, Applied Statistics, 31:115-124 (1982)) were used to test for the normality of the normal samples' Z statistics.

Example 3: Analysis of Polymorphic Loci to Assess Percent Fetal Contribution

To assess fetal nucleic acid proportion in the maternal samples, assays were designed against a set of 192 SNP-containing loci on chromosomes 1 through 12, where two middle oligos differing by one base were used to query each SNP. SNPs were optimized for minor allele frequency in the HapMap 3 dataset. Duan, et al., Bioinformation, 3(3):139-41 (2008); Epub 2008 Nov. 9.

Assays were designed against 576 non-polymorphic loci on each of chr18 and chr21, where each assay consisted of three locus specific oligonucleotides: a left oligo with a 5' universal amplification tail, a 5' phosphorylated middle oligo, and a 5' phosphorylated right oligo with a 3' universal amplification tail. To assess fetal fraction, assays were designed against a set of 192 SNP-containing loci on chr1-12, where two middle oligos, differing by one base, were used to query each SNP. SNPs were optimized for minor allele frequency in the HapMap 3 dataset. Duan, et al., Bioinformation, 3(3):139-41 (2008); Epub 2008 Nov. 9.

Oligonucleotides were synthesized by IDT and pooled together to create a single multiplexed assay pool. PCR products were generated from each subject sample as previously described. Briefly, 8 mL blood per subject was collected into a Cell-free DNA tube (Streck) and stored at room temperature for up to 3 days. Plasma was isolated from blood via double centrifugation and stored at minus 20° C. for up to a year. cfDNA was isolated from plasma using Viral NA DNA purification beads (Dynal), biotinylated, immobilized on MyOne Cl streptavidin beads (Dynal), and annealed with the multiplexed oligonucleotide pool. Appropriately hybridized oligonucleotides were catenated with Taq ligase, eluted from the cfDNA, and amplified using universal PCR primers. PCR product from 96 independent samples was pooled and used as template for cluster amplification on a single lane of a TruSeq v2 SR flow slide (Illumina). The slide was processed on an Illumina HiSeq 2000 to produce a 56-base locus-specific sequence and a 7-base sample tag sequence from an average of 1.18M clusters/sample. Locus-specific reads were compared to expected locus sequences. An average of 1.15M reads (97%) had fewer than 3 mismatches with expected assay structures resulting in an average of 854 reads/locus/sample.

Informative polymorphic loci were defined as loci where fetal alleles differed from maternal alleles. Because the assay exhibits allele specificities exceeding 99%, informative loci were readily identified when the fetal allele proportion of a locus was measured to be between 1 and 20%. A maximum likelihood was estimated using a binomial distribution, such as that described in co-pending application 61/509,188, to determine the most likely fetal proportion based upon measurements from several informative loci. The results correlated well ($R^2>0.99$) with the weighted average approach presented by Chu and colleagues (see, Chu, et al., Prenat. Diagn., 30:1226-29 (2010)).

Example 4: Aneuploidy Detection Using Risk Calculation

The risk of aneuploidy was calculated using an odds ratio that compares a model assuming a disomic fetal chromosome and a model assuming a trisomic fetal chromosome. The distribution of differences in observed and reference proportions were evaluated using normal distributions with a mean of 0 and standard deviation estimated using Monte Carlo simulations that randomly draw from observed data. For the disomic model, $p_o$ was used as the expected reference proportion in the simulations. For the trisomic model, $p_o$ was adjusted on a per sample basis with the fetal proportion adjusted reference proportion $\hat{p}_j$, defined as $$\hat{p}_j = \frac{(1+0.5f_j)p_0}{((1+0.5f_j)p_0)+(1-p_0)}$$

where $f_j$ was the fetal proportion for sample j. This adjustment accounts for the expected increased representation of a test chromosome when the fetus was trisomic. In the simulations both $p_0$ and $f_j$ were randomly chosen from normal distributions using their mean and standard error estimates to account for measurement variances. Simulations are executed 100,000 times. The risk score was defined as the mean trisomy versus disomy odds ratio obtained from the simulations, adjusted by multiplying the risk of trisomy associated with the subject's maternal and gestational age.

Example 5: Results

Chromosome proportion Z Statistics determination. In order to select loci to be used for aneuploidy detection, the subjects of the first cohort were evaluated since their aneuploidy status was known. Six normal, one T18, and one T21 samples (8/171, or 5%) did not meet QC criteria (low count, fetal proportion <3%, and/or evidence from SNPs of a non-singleton pregnancy) and were removed from the dataset. Chromosome proportion Z Statistics were computed in the remaining samples for chr18 and chr21 (FIGS. 3A and 3B). 120/121 (99.2%) disomic samples had Z Statistics <3; one disomic sample had a chr21 Z Statistic of 3.5. 35/35 (100%) T21 and 7/7 (100%) T18 samples had chromosome proportion Z Statistics >3. Thus, using Z Statistic analysis, the assay system utilized in the present invention exhibited 99.2% specificity and 100% sensitivity for T21, and 100% specificity and 100% sensitivity for T18.

Figure 3A:
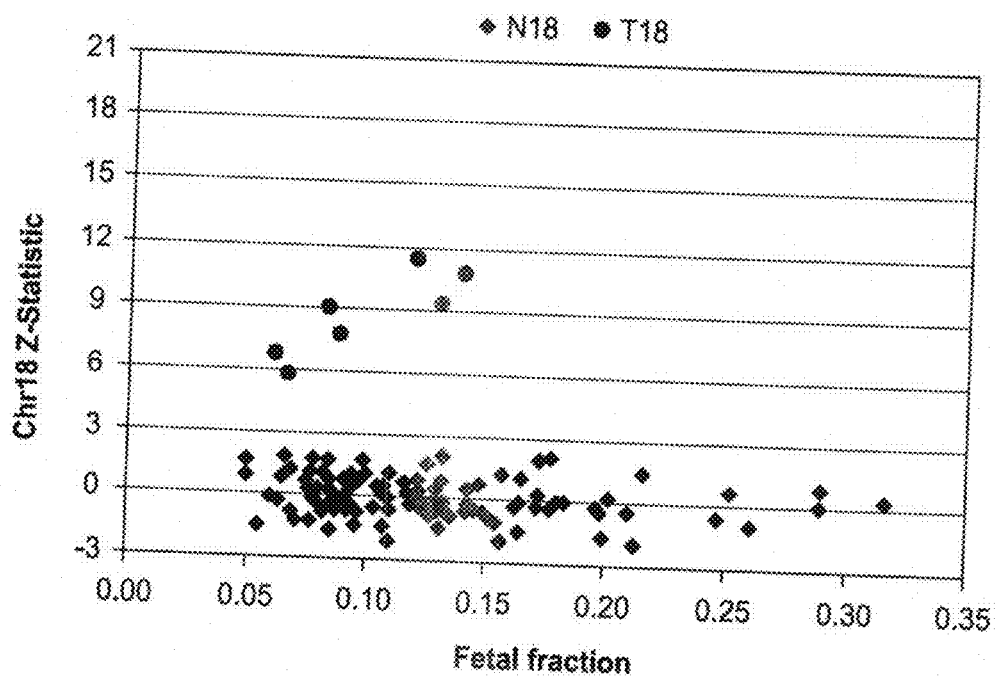
FIGS. 3A and 3B are graphs illustrating the cohort Z statistics versus fetal proportion. The chromosome proportion Z statistic is plotted for chromosome 18 (A) or chromosome 21 (B) versus the fraction of fetal DNA for each cohort subject. Disomic subjects are represented as black diamonds, trisomic subjects as grey diamonds.
Figure 3B:
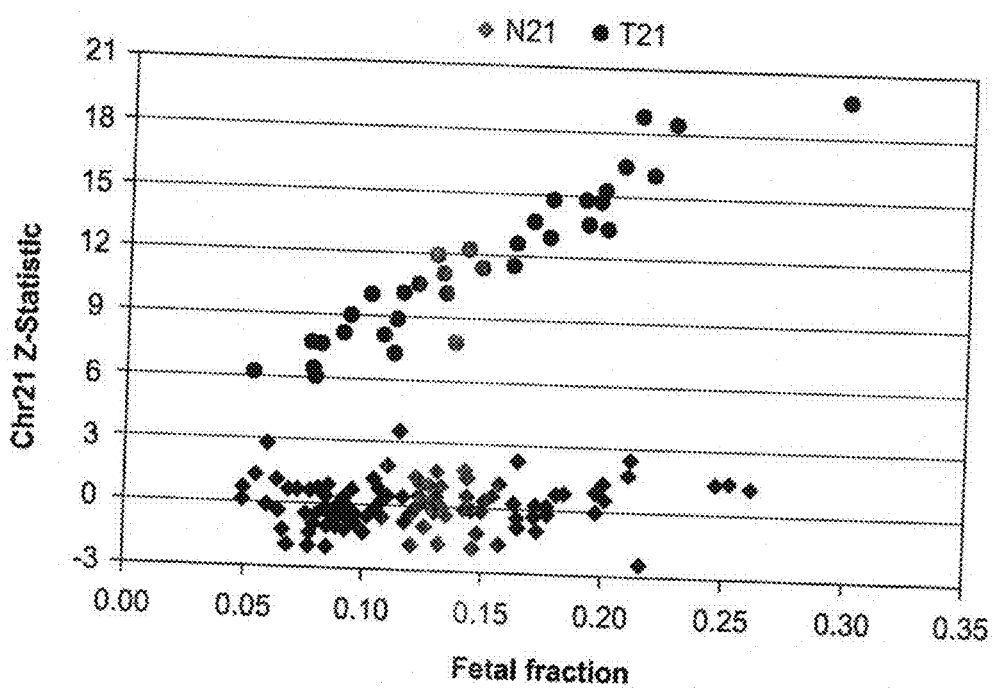

In order to measure fetal proportion reliably, 192 assays targeting SNPs were incorporated into a multiplex assay pool. By measuring fetal proportion and chromosome proportion in the same reaction, estimates of fetal proportion from polymorphic assays were ensured to closely represent fetal proportion in the non-polymorphic assays used to assess chromosome proportion. Fetal proportion exhibited a strong correlation ($R^2>0.90$) with the chromosome proportion Z Statistic in aneuploid pregnancies (FIGS. 3A and 3B).

Importantly, the Z Statistic was not responsive to fetal proportion in normal pregnancies, reflecting a major limitation of the Z Statistic metric: samples with low Z Statistic values arise from both euploid samples and aneuploid samples with modest fetal proportion. It was reasoned that a metric that was responsive to fetal proportion in euploid as well as aneuploid pregnancies would be preferable. Thus a risk calculation was developed that leverages fetal proportion information to (1) define expected chromosome dosages for trisomic versus disomic test chromosomes, and (2) compute the odds that a sample belongs to one or the other group.

Figure 4A:
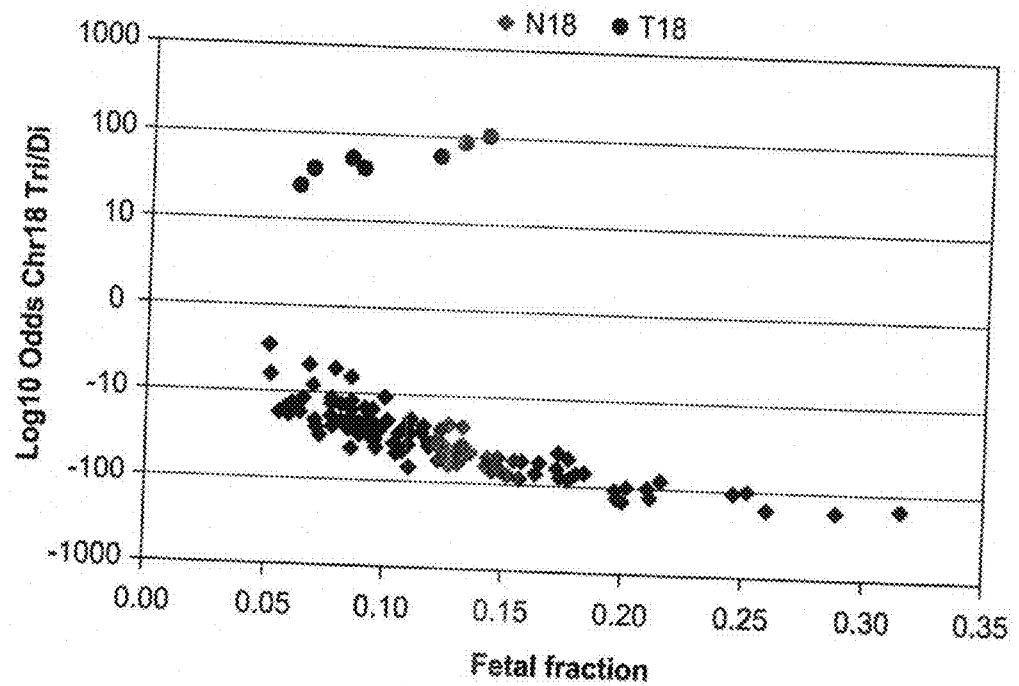
FIGS. 4A and 4B are graphs illustrating the cohort risk calculation odds versus fetal proportion. The risk-computed odds of trisomy versus disomy for chromosome 18 (A) or chromosome 21 (B) are plotted versus the fraction of fetal DNA for each cohort subjects. Disomic subjects are represented as black diamonds, trisomic subjects as grey diamonds.
Figure 4B:
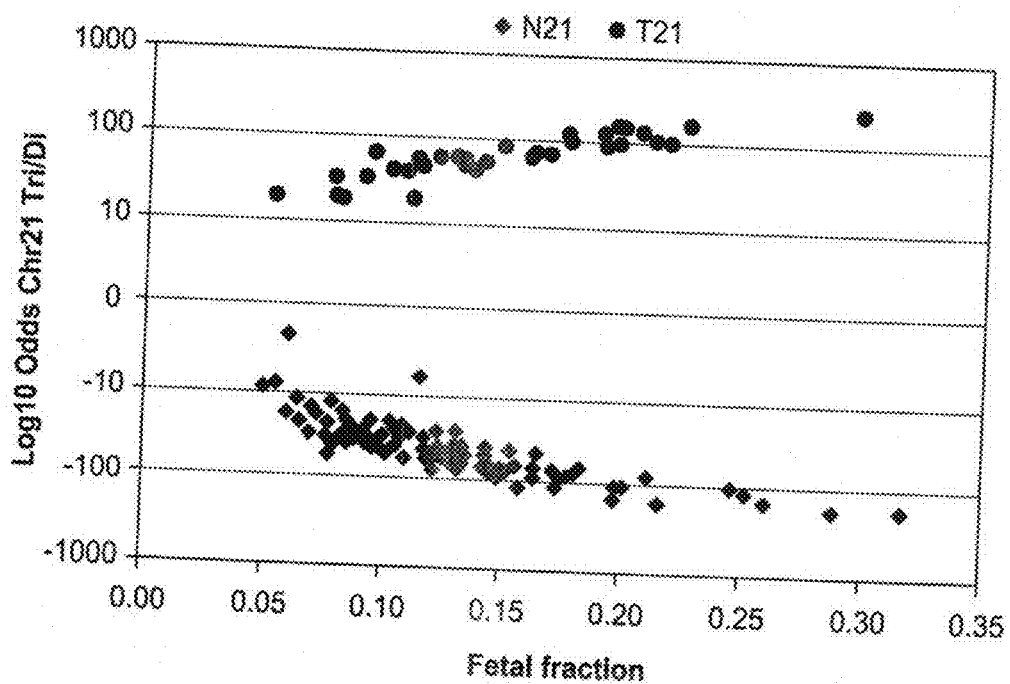

Analysis of cohort using the risk calculation. The risk calculation was used to compute the odds of trisomy versus disomy of chr18 and chr21 in each sample within the first cohort (FIGS. 4A and 4B). As expected, the risk calculation odds of the present invention demonstrated a response to fetal proportion in both trisomic and disomic samples, and the response magnitude was approximately equivalent in the two groups. The risk calculation of the present invention correctly discriminated all euploid from aneuploid samples, and the difference between the lowest aneuploid odds and the euploid odds exceeded $10^{12}$. All aneuploidy samples had odds $>10^{10}$.

Figure 5A:
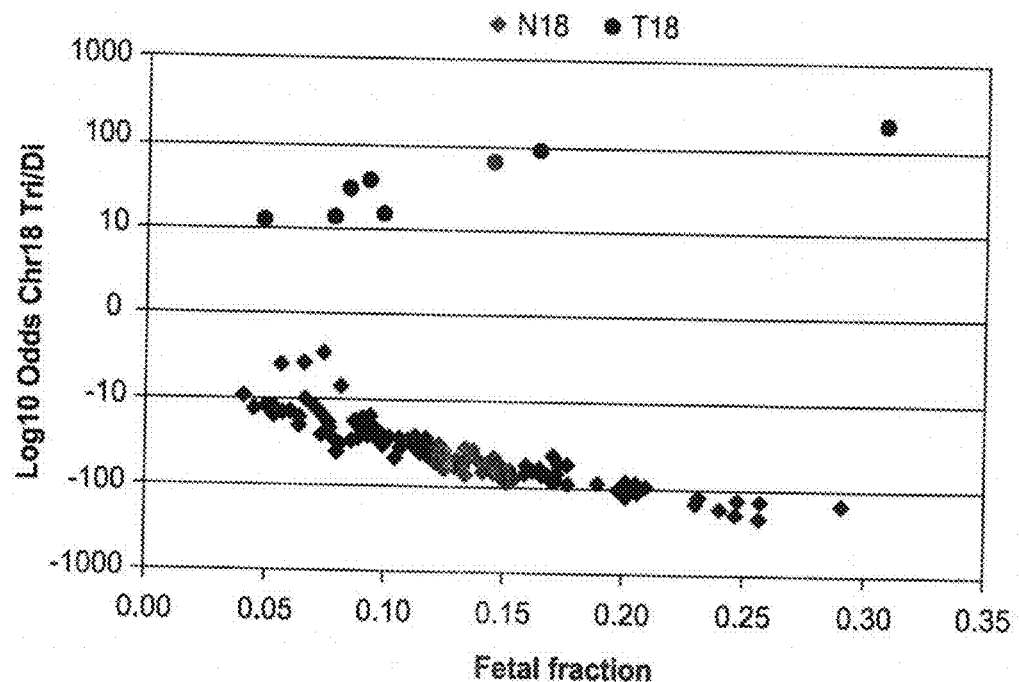
FIGS. 5A and 5B are graphs illustrating the blinded (second) cohort risk calculation odds of the present invention versus fetal proportion. The risk-computed odds of trisomy versus disomy for chromosome 18 (A) or chromosome 21 (B) are plotted versus the fraction of fetal DNA for each blinded (second) cohort subject. Disomic subjects are represented as black diamonds, trisomic subjects as grey diamonds.
Figure 5B:
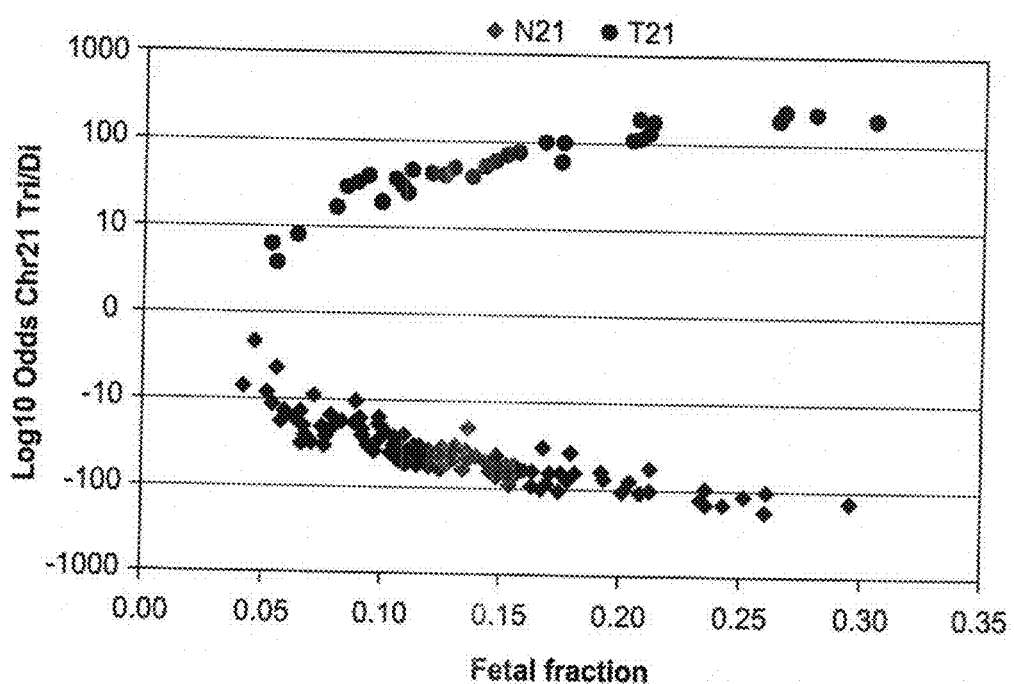

Second of risk calculation analysis on a blinded cohort. In order to test the performance of the assay and risk calculation of the present invention in an independent set of subjects, a blinded second cohort consisting of 123 normal, 36 T21, and 8 T18 pregnancies was assayed. All samples passed QC criteria and were assigned risk calculation odds scores for chr18 and chr21 (FIGS. 5A and 5B). As above, the risk calculation of the present invention correctly discriminated all trisomy from disomy subjects. The difference between the lowest aneuploid odds and the highest euploid odds was $10^{39}$. All 36 T21 and 8 T18 samples had trisomy odds exceeding $10^{2.67}$ (>99.8% risk of trisomy).

Current prenatal aneuploidy screening tests employ risk thresholds of approximately 1 in 300 ($10^{-2.5}$) for referral to invasive testing. If this threshold were applied to the risk calculation odds for the blinded cohort, it would yield 99.2% specificity and 100% sensitivity for each chromosome. This compares favorably with current screening methods, which can entail a 5% false positive and 10% false negative rate. Moreover, because the minimum difference between the euploid and aneuploid subjects' risk calculation odds was almost four orders of magnitude for T21 and fourteen orders of magnitude for T18, a variety of thresholds produce perfect sensitivity and specificity.

By generating sequencing template from chromosome-specific assays and by producing high mapping rates, the chromosome-selective assay employed herein permits aneuploidy detection using ~1M raw reads per subject, enabling analysis of 96 subjects per sequencing lane. By contrast, MPSS evaluates the entire genome, and requires ~25M raw reads per subject, which limits sequencing throughput to 4-6 samples per lane. Thus, the present methods employing chromosome selective assays and simultaneous interrogation of polymorphic and non-polymorphic loci in multiplexed reactions enjoys a >20-fold advantage over MPSS in sequencing cost and throughput.

The present assay's capacity for genotyping individual polymorphic loci permits simultaneous determination of fetal proportion and chromosome proportion. Fetal proportion information was leveraged by imposing a QC requirement that each sample have at least 3% fetal DNA, thereby avoiding low confidence calls arising from low proportions of fetal DNA. In addition, the risk calculation algorithm was developed to produce a fetal proportion-dependent risk score indicating the odds of a sample being trisomic versus disomic.

The risk calculation analysis of the present invention differs from chromosome proportion Z Statistic analysis in several important respects. First, because 96 samples are processed in a single batch/lane, the risk calculation leverages the observed variances within and between samples in a lane, rather than estimating variance based upon information obtained from a previously-analyzed reference dataset. Thus, the risk calculation of the present invention is less susceptible to process drift and does not require external reference samples or normalizing adjustments based upon historical information.

Second, the risk calculation employed herein is responsive to fetal proportion in both the trisomic and disomic state, whereas Z Statistic is only responsive to fetal proportion in the trisomic state. As a consequence, the risk calculation of the present invention produces overall better separation of trisomic versus disomic samples. Moreover, because samples with low fetal proportion yield odds with lower magnitudes in both disomic and trisomic samples, the risk calculation of the present invention communicates a more accurate understanding of the confidence with which a call is being made in disomic samples as well as trisomic samples.

Third, because the risk of aneuploidy varies significantly with maternal and gestational age—and because incorporating these risks is standard practice in reporting screening results—the risk calculation of the present invention is designed to accommodate incorporation of age-related risks. Specifically, because both the risk computed from the chromosome-selective assay and age-related risk reflect a subject's odds of trisomy versus disomy, these risk components are readily combined. By contrast, the Z Statistic reflects the likelihood that a sample is disomic, and therefore is not readily combined with age related risks of trisomy versus disomy. One consequence of this deficiency is that the Z Statistic will exhibit different performance depending upon a subject's age. For example, an 18 year old subject at 12 weeks' gestation and with a Z Statistic of 3 is ~38 times more likely to be a false positive than a 44 year old subject at 12 weeks' gestation and with the same score.

The chromosome-selective assays used herein enable highly-multiplexed sequencing of polymorphic and non-polymorphic loci from specific chromosomes of interest in up to 96 samples simultaneously. The risk calculation of the present invention analyzes resulting chromosome dosage and fetal proportion information to provide an individualized assessment of trisomy versus disomy risk which can be combined with other risk information. In this study, the risk calculation methods of the invention correctly discriminated all T21 and T18 cases from euploid cases in both a first cohort and a blinded second cohort.

Example 6: Aneuploidy Detection

The risk calculation algorithm used in calculation of the estimated risk of aneuploidy used an odds ratio comparing a mathematic model assuming a disomic fetal chromosome and a mathematic model assuming a trisomic fetal chromosome. When $x_1 = p_j - p_0$ is used to describe the difference of the observed proportion $p_j$ for sample j and the estimated reference proportion $p_0$, the risk calculation algorithm used computed:

$$\frac{P(x_j \mid T)}{P(x_j \mid D)},$$

where T was the trisomic model and D was the disomic model. The disomic model D was a normal distribution with mean 0 and a sample specific standard deviation estimated by Monte Carlo simulations as described below. The trisomic model T was also a normal distribution with mean 0, determined by transforming $x_j$ to $\hat{x}_j = p_j - \hat{p}_j$, the difference between the observed proportion and a fetal fraction adjusted reference proportion as defined by:

$$\hat{p}_j = \frac{(1 + 0.5 f_j) p_0}{(1 + 0.5 f_j) p_o + (1 - p_0)},$$

where $f_j$ was the fetal fraction for sample j. This adjustment accounted for the expected increased representation of a trisomic fetal chromosome. Monte Carlo simulations were used to estimate sample specific standard deviations for disomic and trisomic models of proportion differences. Observed proportions for each sample were simulated by non-parametric bootstrap sampling of loci and calculating means, or parametric sampling from a normal distribution using the mean and standard error estimates for each chromosome from the observed non-polymorphic locus counts. Similarly, the reference proportion $p_o$ and fetal fraction $f_j$ were simulated by non-parametric sampling of samples and polymorphic loci respectively, or chosen from normal distributions using their mean and standard error estimates to account for measurement variances. Parametric sampling was used in this study. Simulations were executed 100,000 times, and proportion differences were computed for each execution to construct the distributions. Based on the results of these simulations, normal distributions were found to be good models of disomy and trisomy.

The final risk calculation algorithm risk score is defined as:

$$\frac{P(x_j \mid T) P(T)}{P(x_j \mid D) P(D)}$$

where P(T)/P(D) is the prior risk of trisomy vs. disomy. The data on prior risk of aneuploidy was taken from well-established tables capturing the risk of trisomy associated with the subject's maternal and gestational age (Nicolaides, Ultrasound Obstet Gynecol, 21:313-321 (2003)).

While this invention is satisfied by aspects in many different forms, as described in detail in connection with preferred aspects of the invention, it is understood that the present disclosure is to be considered as exemplary of the principles of the invention and is not intended to limit the invention to the specific aspects illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

The invention claimed is:

1. A method to calculate a risk that a first fetal chromosome in a maternal sample from a pregnant female comprising maternal and fetal nucleic acids is aneuploid, the method comprising:
    providing first one or more sequence-specific oligonucleotide probes directed to a plurality of non-polymorphic loci on each of at least a first and second chromosome;
    providing second one or more sequence-specific oligonucleotide probes directed to a plurality of polymorphic loci on at least a third chromosome;
    amplifying the plurality of non-polymorphic and polymorphic loci using the first and second sequence-specific oligonucleotide probes;
    determining a number of each amplified non-polymorphic locus on the at least first and second chromosomes;
    determining a number of alleles at each amplified polymorphic locus on the at least third chromosome;
    estimating a chromosome frequency for the at least first and second chromosomes based on the number of amplified non-polymorphic loci on the at least the first and second chromosomes; calculating a fetal nucleic acid proportion in the maternal sample based on the number of alleles at the amplified polymorphic loci;
    calculating a value of likelihood that the first fetal chromosome is disomic using the fetal nucleic acid proportion to adjust the estimated chromosome frequency of the first and second chromosomes;
    calculating a value of likelihood that the first fetal chromosome is aneuploid using the fetal nucleic acid proportion to adjust the estimated chromosome frequency of the first and second chromosomes; and
    calculating the risk of a fetal aneuploidy of the first fetal chromosome by comparing the values of likelihood to a first mathematic model assuming a disomic first fetal chromosome and a second mathematic model assuming an aneuploid first fetal chromosome.

2. The method of claim 1, wherein the calculated risk is an odds ratio comparing the first mathematic model assuming a disomic first fetal chromosome and a second mathematic model assuming a trisomic first fetal chromosome.

3. The method of claim 1, wherein the fetal nucleic acid proportion is determined using the frequency of alleles on two or more chromosomes in the maternal sample.

4. The method of claim 1, wherein the fetal aneuploidy is a result of one or no copies of a chromosome or part of a chromosome.

5. The method of claim 1, wherein the fetal aneuploidy is a result of three or more copies of a chromosome or part of a chromosome.

6. The method of claim 1, wherein the maternal sample is maternal plasma or serum.

7. The method of claim 1, further comprising a step of adjusting the calculated risk using extrinsic information on prior risk.

8. The method of claim 1, further comprising a step of adjusting the calculated risk using information on prior risk associated with maternal age or gestational age.

9. The method of claim 1, further comprising the step of identifying a set of non-polymorphic loci best able to discriminate trisomy samples from normal samples.

10. A method to calculate a risk that a first fetal chromosome in a maternal sample from a pregnant female comprising maternal and fetal nucleic acids is aneuploid, the method comprising:
    providing first one or more sequence-specific oligonucleotide probes directed to a plurality of non-polymorphic loci on each of at least a first and second chromosome;
    providing second one or more sequence-specific oligonucleotide probes directed to a plurality of polymorphic loci on at least a third chromosome;
    amplifying the plurality of non-polymorphic and polymorphic loci using the first and second sequence-specific oligonucleotide probes;
    determining a number of each amplified non-polymorphic locus on the at least first and second chromosomes;
    determining a number of alleles at each amplified polymorphic locus on the at least third chromosome;
    estimating a chromosome frequency for the at least first and second chromosomes based on the number of the amplified non-polymorphic loci on the at least the first and second chromosomes;
    calculating a fetal nucleic acid proportion in the maternal sample based on the number of alleles at the amplified polymorphic loci;
    calculating a value of likelihood that the first fetal chromosome is disomic;
    calculating a value of likelihood that the first fetal chromosome is aneuploid using the fetal nucleic acid proportion in the maternal sample to adjust the estimated chromosome frequency of the first and second chromosomes;
    calculating the risk of a fetal aneuploidy of the first fetal chromosome by comparing the values of likelihood to a first mathematic model assuming a disomic first fetal chromosome and a second mathematic model assuming an aneuploid first fetal chromosome; and
    adjusting the calculated risk using extrinsic information on prior risk.

11. The method of claim 10, wherein the calculated risk is an odds ratio comparing the first mathematic model assuming a disomic first fetal chromosome and a second mathematic model assuming a trisomic first fetal chromosome.

12. The method of claim 10, wherein the fetal nucleic acid proportion is determined using the frequency of alleles on two or more chromosomes in the maternal sample.

13. The method of claim 10, wherein the fetal aneuploidy is a result of one or no copies of a chromosome or part of a chromosome.

14. The method of claim 10, wherein the fetal aneuploidy is a result of three or more copies of a chromosome or part of a chromosome.

15. The method of claim 10, wherein the maternal sample is maternal plasma or serum.

16. The method of claim 10, further comprising a step of adjusting the calculated risk using extrinsic information on prior risk.

17. The method of claim 10, further comprising a step of adjusting the calculated risk using information on prior risk associated with maternal age or gestational age.

18. The method of claim 10, further comprising the step of identifying a set of non-polymorphic loci best able to discriminate trisomy samples from normal samples.

19. A method to calculate a risk that a first fetal chromosome in a maternal sample from a pregnant female comprising maternal and fetal nucleic acids is triploid, the method comprising:

providing first one or more sequence-specific oligonucleotide probes directed to a plurality of non-polymorphic loci on each of at least a first and second chromosome;

identifying a set of non-polymorphic loci best able to discriminate trisomy samples from normal samples;

providing second one or more sequence-specific oligonucleotide probes directed to a plurality of polymorphic loci on at least a third chromosome;

amplifying a plurality of non-polymorphic loci using the identified non-polymorphic loci best able to discriminate trisomy samples from normal samples and amplifying a plurality of polymorphic loci using the first and second sequence-specific oligonucleotide probes;

determining a number of each amplified non-polymorphic locus on the at least first and second chromosomes;

determining a number of alleles at each amplified polymorphic locus on the at least third chromosome;

estimating a chromosome frequency for the at least first and second chromosomes based on the number of amplified non-polymorphic loci on the at least the first and second chromosomes;

calculating a fetal nucleic acid proportion in the maternal sample based on the number of alleles at the amplified polymorphic loci;

calculating a value of likelihood that the first fetal chromosome is disomic using the fetal nucleic acid proportion to adjust the estimated chromosome frequency of the first and second chromosomes;

calculating a value of likelihood that the first fetal chromosome is triploid using the fetal nucleic acid proportion to adjust the estimated chromosome frequency of the first and second chromosomes; and calculating the risk of a fetal trisomy of the first fetal chromosome by comparing the values of likelihood to a first mathematic model assuming a disomic first fetal chromosome and a second mathematic model assuming an triploid first fetal chromosome.

20. The method of claim 19, wherein the fetal nucleic acid proportion is determined using the frequency of alleles on two or more chromosomes in the maternal sample.

* * * * *